(12) United States Patent
Shekhar et al.

(10) Patent No.: US 10,426,345 B2
(45) Date of Patent: Oct. 1, 2019

(54) SYSTEM FOR GENERATING COMPOSITE IMAGES FOR ENDOSCOPIC SURGERY OF MOVING AND DEFORMABLE ANATOMY

(71) Applicant: Children's National Medical Center, Washington, DC (US)

(72) Inventors: Raj Shekhar, Elkridge, MD (US); Xin Kang, Hyattsville, MD (US); Mahdi Azizian, Washington, DC (US); Timothy Kane, Washington, DC (US); Craig Peters, McLean, VA (US)

(73) Assignee: Children's National Medical Center, Washington, DC (US)

( * ) Notice: Subject to any disclaimer, the term of this patent is extended or adjusted under 35 U.S.C. 154(b) by 942 days.

(21) Appl. No.: 14/245,721

(22) Filed: Apr. 4, 2014

(65) Prior Publication Data

US 2014/0303491 A1 Oct. 9, 2014

Related U.S. Application Data

(60) Provisional application No. 61/940,915, filed on Feb. 18, 2014, provisional application No. 61/808,329, filed on Apr. 4, 2013.

(51) Int. Cl.
*A61B 5/00* (2006.01)
*A61B 5/06* (2006.01)
(Continued)

(52) U.S. Cl.
CPC .......... *A61B 5/0035* (2013.01); *A61B 1/0005* (2013.01); *A61B 1/00009* (2013.01);
(Continued)

(58) Field of Classification Search
CPC .............. A61B 1/00009; A61B 1/0005; A61B 1/00193; A61B 1/3132; A61B 2034/2055;
(Continued)

(56) References Cited

U.S. PATENT DOCUMENTS

| 2003/0088179 A1* | 5/2003 | Seeley | A61B 6/12 600/424 |
|---|---|---|---|
| 2005/0085718 A1* | 4/2005 | Shahidi | A61B 1/04 600/424 |

(Continued)

OTHER PUBLICATIONS

Office Action dated Feb. 2, 2017 in European Patent Application No. 14778175.1.
(Continued)

*Primary Examiner* — Ruth S Smith
(74) *Attorney, Agent, or Firm* — Oblon, McClelland, Maier & Neustadt, L.L.P.

(57) ABSTRACT

A device for generating composite images of dynamically changing surgical anatomy includes circuitry configured to receive, from an endoscopic imaging device, endoscopic image data. The circuitry is configured to receive, from a tomographic imaging device, intra-operative tomographic image data. The circuitry is configured to receive, from a tracking device, spatial tracking data corresponding to the endoscopic imaging device and the tomographic imaging device. The circuitry is configured to generate real-time dynamically changing composite image data by overlaying, based on the spatial tracking data, the intra-operative tomographic image data on the endoscopic image data. The circuitry is configured to output the composite image data to a display.

6 Claims, 22 Drawing Sheets

(51) Int. Cl.

| | |
|---|---|
| *A61B 1/00* | (2006.01) |
| *A61B 1/313* | (2006.01) |
| *A61B 8/00* | (2006.01) |
| *A61B 8/08* | (2006.01) |
| *G06T 7/33* | (2017.01) |
| *G06T 7/38* | (2017.01) |
| *A61B 8/12* | (2006.01) |
| *A61B 34/20* | (2016.01) |
| *A61B 90/00* | (2016.01) |

(52) U.S. Cl.
CPC ........ *A61B 1/00193* (2013.01); *A61B 1/3132* (2013.01); *A61B 5/0073* (2013.01); *A61B 5/066* (2013.01); *A61B 5/7425* (2013.01); *A61B 8/4209* (2013.01); *A61B 8/4245* (2013.01); *A61B 8/4416* (2013.01); *A61B 8/483* (2013.01); *A61B 8/5261* (2013.01); *A61B 8/587* (2013.01); *G06T 7/337* (2017.01); *G06T 7/38* (2017.01); *A61B 5/062* (2013.01); *A61B 8/12* (2013.01); *A61B 8/4254* (2013.01); *A61B 2034/2055* (2016.02); *A61B 2090/365* (2016.02); *A61B 2090/371* (2016.02); *A61B 2090/378* (2016.02); *G06T 2207/10021* (2013.01); *G06T 2207/10081* (2013.01); *G06T 2207/10104* (2013.01); *G06T 2207/10108* (2013.01); *G06T 2207/10136* (2013.01); *G06T 2207/30056* (2013.01); *G06T 2207/30084* (2013.01)

(58) Field of Classification Search
CPC ........ A61B 2090/365; A61B 2090/371; A61B 2090/378; A61B 5/0035; A61B 5/0073; A61B 5/062; A61B 5/066; A61B 5/7425; A61B 8/12; A61B 8/4209; A61B 8/4245; A61B 8/4254; A61B 8/4416; A61B 8/483; A61B 8/5261; A61B 8/587; G06T 2207/10021; G06T 2207/10081; G06T 2207/10104; G06T 2207/10108; G06T 2207/10136; G06T 2207/30056; G06T 2207/30084; G06T 7/337; G06T 7/38
See application file for complete search history.

(56) References Cited

U.S. PATENT DOCUMENTS

| | | | |
|---|---|---|---|
| 2005/0285038 A1* | 12/2005 | Frangioni | A61B 5/0059 250/330 |
| 2006/0098864 A1* | 5/2006 | Ziel | G01S 7/52068 382/154 |
| 2008/0030578 A1 | 2/2008 | Razzaque et al. | |
| 2008/0071143 A1* | 3/2008 | Gattani | A61B 1/00009 600/117 |
| 2009/0097723 A1* | 4/2009 | Washburn | A61B 8/06 382/128 |
| 2009/0225324 A1 | 9/2009 | Bernstein et al. | |
| 2010/0167250 A1* | 7/2010 | Ryan | G09B 23/285 434/267 |
| 2011/0044521 A1* | 2/2011 | Tewfik | G06K 9/6206 382/131 |
| 2012/0046521 A1 | 2/2012 | Hunter et al. | |
| 2012/0101370 A1 | 4/2012 | Razzaque et al. | |
| 2013/0345514 A1 | 12/2013 | Manion | |

OTHER PUBLICATIONS

International Preliminary Report on Patentability and Written Opinion dated Sep. 23, 2014 in PCT/US2014/033045.
Nathaniel J. Soper, et al., "Laparoscopic Cholecystectomy: Complications and Management"; The SAGES Manual of Quality, Outcomes and Patient Safety, pp. 231-240.
F. Volonte, et al.; "Console-Integrated Stereoscopic OsiriX 3D Volume-Rendered Images for da Vinci Colorectal Robotic Surgery"; Surgical Innovation; pp. 158-163.
Zhengyou Zhang; "A Flexible New Technique for Camera Calibration"; IEEE Transactions on Pattern Analysis and Machine Intelligence 22(11):1330-1334, 2000; 22 pages.
Ziv Yaniv, et al., Ultrasound Calibration Framework for the Image-Guided Surgery Toolkit (IGSTK); Medical Imaging 2011: Visualization, Image-Guided Procedures, and Modeling; Proc. of SPIE 7964:79641N; 11 pages.
A. Hostettler, et al.; "A Real-Time Predictive Simulation of Abdominal Viscera Positions During Quiet Free Breathing"; Progress in Biophysics and Molecular Biology 103 (2010) 169-184; pp. 169-184.
Communication pursuant to Article 94(3) EPC dated Jan. 18, 2018 in European Patent Application No. 14 778 175.1.
Office Action dated Sep. 19, 2018 in European Patent Application No. 14 778 175.1.
Office Action dated Jul. 2, 2019, in European Patent Application No. 14 778 175 .1-1008. (3 pgs.)

\* cited by examiner

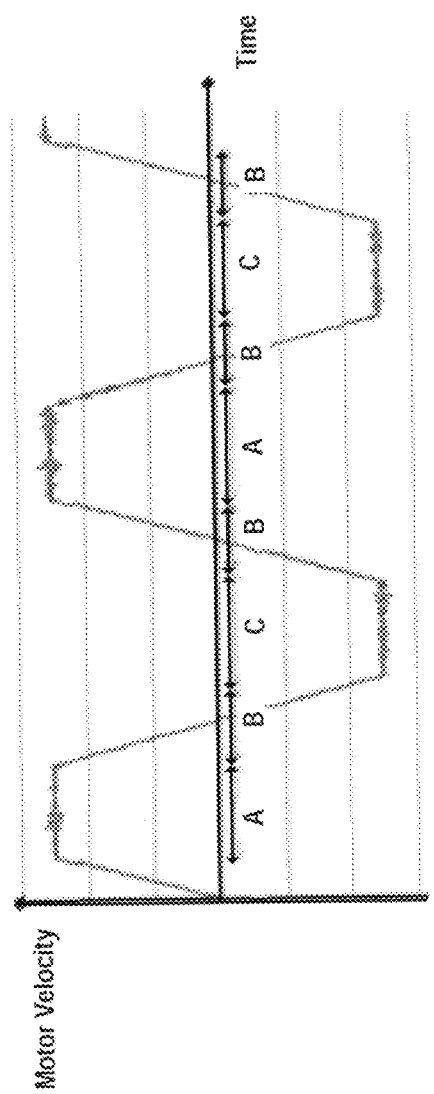

SYSTEM FOR GENERATING COMPOSITE IMAGES FOR ENDOSCOPIC SURGERY OF MOVING AND DEFORMABLE ANATOMY

CROSS REFERENCE TO RELATED APPLICATIONS

This application claims the benefit of priority of U.S. Patent Application No. 61/940,915, filed Feb. 18, 2014, and U.S. Patent Application No. 61/808,329, filed Apr. 4, 2013 the entire contents of all are incorporated herein by reference.

BACKGROUND

Technical Field

Among other things, the present disclosure is related to minimally invasive surgeries that are carried out under the guidance of real-time video produced by a flexible or rigid endoscope. The present disclosure pertains specifically to combining multiple representations (e.g., medical images or parameters derived from them) of the surgical anatomy to give minimally invasive surgeons a comprehensive view of the surgical field. Whereas one of the representations may be endoscopic video, other representations may be tomographic images acquired both before and/or during surgery. The present disclosure further pertains to a system and methods that permit creating composite images in real-time and in the operating room (OR) during live surgeries.

REFERENCES

The references listed below are cited in the present disclosure and are incorporated herein by reference.
[1] N. J. Soper, and B. F. Santos (2012): Laparoscopic Cholecystectomy: Complications and Management. The SAGES Manual of Quality, Outcomes and Patient Safety, 231-240.
[2] F. Volonte, F. Pugin, N. C. Buchs, J. Spaltenstein, M. Hagen, O. Ratib, P. Morel (2012): Console-Integrated Stereoscopic OsiriX 3D Volume-Rendered Images for da Vinci Colorectal Robotic Surgery, Surgical Innovation.
[3] Zhang, Z. (2000) A flexible new technique for camera calibration. IEEE Trans Pattern Anal Machine Intell 22(11):1330-1334.
[4] Yaniv, Z.; Foroughi, P.; Kang, H-J; Boctor, E. (2011) Ultrasound calibration framework for the image-guided surgery toolkit. Medical Imaging 2011: Visualization, Image-Guided Procedures, and Modeling, Proc. of SPIE 7964:79641N-1-11.
[5] Hostettler, A.; Nicolau, S. A.; Rémond, Y.; Marescaux, J.; Soler, L. (2010) A real-time predictive simulation of abdominal viscera positions during quiet free breathing, Progress in biophysics and molecular biology 103(2-3): 169-184.

DESCRIPTION OF RELATED ART

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly nor impliedly admitted as prior art against the present disclosure.

Minimally invasive surgeries are an attractive alternative to conventional open surgeries and are known to improve outcomes, cause less scarring, and lead to significantly faster patient recovery. For certain surgical procedures, such as cholecystectomy, they have become the standard of care.

Despite this success and the increasing application of minimally invasive surgery to treat or correct various pathologic conditions, visualization of the surgical field is more challenging in endoscopic surgery than in open surgery. Endoscopic video is rich in surface detail but provides no information on structures beneath the exposed organ surfaces. Furthermore, standard endoscopic video, often monocular, does not give a surgeon a good appreciation of depth and 3D spatial relationships among anatomical structure. Compared with open procedures, the lack of tactile feedback in laparoscopic procedures creates a greater need for enhanced intraoperative visualization for achieving safe and effective surgical outcomes.

These limitations could be a source of major complications, which, for laparoscopic cholecystectomy, is reported to be up to 1.74% [1]. These limitations could further be attributed to minimally invasive surgeries being a relatively small share of all surgeries. In 2007, only 16.5% surgeries (only 3.3 million of approximately 20 million surgeries) in the United States annually were performed in a minimally invasive manner. The present disclosure is aimed at reducing the current rate of complications and resulting trauma, and increasing the precision and overall share of minimally invasive surgeries by increasing the visual information normally available to the operating surgeons.

One of the approaches to enrich visual information is to combine data from multiple imaging modalities that often contain complementary information. A challenge in doing so is the dynamic nature of the surgical anatomy. In particular, the soft-tissue organs being operated on move and deform due to surgical manipulations. One approach to address this challenge is to acquire images in real-time during the surgery. However, not all imaging modalities are appropriate for use in the OR. For example, it is difficult to perform positron emission tomography (PET) intra-operatively; however, there are instances in which combining the PET data with endoscopic video may aid the surgeon. Special methods are needed if pre-operative images are also a part of image composition.

Laparoscopic ultrasound (LUS) can provide real-time intra-operative images without the risk of ionizing radiation. An advantage of using live intra-operative images in combination with live endoscopic video is that soft-tissue deformation does not need to be modeled, and accurate image-to-video registration can be accomplished with standard tracking methods.

In addition to the laparoscopic ultrasound limitation of only showing 2D cross-sections of the 3D, its use has another limitation in that it necessitates creating an additional port and an extra hand to operate related devices. Mitigating these limitations is desirable for improved workflow in an OR environment.

SUMMARY

Visual information is critical to safe and effective surgical outcomes in minimally invasive endoscopic surgical procedures in which the operative field is often not directly visualized and haptic feedback is limited. The visual information that is generally available comes in the form of continuous video images of the operative field produced by conventional endoscopes. Although real-time, conventional endoscopic video images provide a flat representation of the 3D operative field and are incapable of visualizing internal structures located beneath organ surfaces. Computed tomography (CT) and magnetic resonance (MR) images are difficult to fuse in real time with laparoscopic views due to the deformable nature of soft-tissue organs.

Among other things, the present disclosure addresses the inability to visualize internal structures not seen by the endoscopic camera by creating composite images by augmenting the endoscopic video with 2D or 3D tomographic images of the surgical anatomy. Tomographic images provide cross-sectional views of the anatomy and thus reveal internal structures not visible in the video images. Depending on when the tomographic imaging is performed, whether before surgery or during surgery, the method of image composition may differ. Unlike conventional systems, the present disclosure describes automatic composition methods applicable for both pre- and intra-operative tomographic images.

Utilizing emerging camera technology, a system according to the present disclosure provides a real-time stereoscopic augmented reality (AR) system for laparoscopic surgery by merging live laparoscopic ultrasound image data with stereoscopic video. The system creates two new visual cues—(1) perception of true depth with improved understanding of 3D spatial relationships among anatomical structures, and (2) visualization of critical internal structures along with a more comprehensive visualization of the operating field.

In certain embodiments, the LUS image data may be 2D, which presents challenges when generating composite streams using a combination stereoscopic video overlaid with the LUS image data. Specifically, although the two modalities do contain complementary data, the ultrasound images are a 2D cross-section of a 3D scene while the laparoscopic video is a projection image of the 3D scene. An overlay of these fundamentally different image formats makes the resulting AR difficult to interpret for laparoscopic surgeons. An improved multimodality surgical visualization, wherein 3D ultrasound images are combined with laparoscopic video, is enabled by a system according to embodiments of the present disclosure. It should be noted that the intraoperative 3D ultrasound data can also be used to augment the vision of a surgeon during open surgical procedures.

Embodiments of a stereoscopic AR system according to the present disclosure have been developed for near-term clinical translation with seamless integration into the existing surgical workflow. Embodiments include a stereoscopic vision device, a LUS device, and an optical tracking device. Processing circuitry executing specialized software instructions processes streams of imaging data from the tracked devices and registers those in real time. The resulting two ultrasound-augmented video streams (one each for left and right eyes) give a live stereoscopic AR view of the operating field.

In one or more embodiments, a composite image generation device or system according to the present disclosure uses stereoscopic endoscopes based on 3D camera technology. Stereoscopic endoscopes provide two separate video streams—one each for the observer's left eye and the right eye. When viewed on an appropriate 3D display device, the resulting images give the observer a perception of depth and an enhanced understanding of 3D spatial relationship among anatomic structures. Studies suggest that being able to see the surgical field in 3D rather than in 2D provides clear advantages in terms of greater surgical efficiency (and hence reduced procedure time) and acceleration of the learning curve [2].

In one or more embodiments, LUS image data utilized for generating composite AR streams is received from an ultrasound imager implemented within an OR table. Such a capability permits continuous hands-free volumetric scanning of the patient lying on the OR table and provides the operating surgeon an unprecedented level of detail, in real time, of the surgical field. The availability of volumetric data may also ease the interpretation problem of conventional ultrasound images and allow presenting to operating surgeons 3D rendered views and reformatted cross-sectional views different from the acquisition planes.

In certain embodiments, the 3D acquisition of LUS image data is accomplished by mechanically steering an ultrasound transducer mounted on the slider of a linear stage or multiple linear stages. The reconstructed volumetric images are updated and rendered at a regular frequency desired by the operating surgeon. This frequency could be as fast as the rate of 2D ultrasound image acquisition. In certain embodiments, it is possible to use a matrix (3D) ultrasound transducer that either eliminates linear scanning or allows reconstructing larger volumes with linear scanning. The concept of intra-operative imaging described herein is particularly suitable for children because ultrasound is radiation-free and provides higher-quality images in small patients.

For multimodality intraoperative visualization during laparoscopic procedures, by spatially tracking the 3D ultrasound scanner and the laparoscope, a view-dependent rendering of the ultrasound volume can be created and overlaid on live stereoscopic video of the surgical field. In open surgeries, the surgeon's eyes can be tracked to overlay 3D ultrasound information on the surgeon's view of the patient. In this embodiment, the surgeon may wear a head-mounted display, such as Google Glass®, or similar viewing devices.

To demonstrate the results of an embodiment of a stereoscopic AR system according to the present disclosure, a series of stereoscopic AR interrogations were conducted on the liver, gall bladder, biliary tree, and kidneys in two swine. The preclinical studies demonstrated the feasibility of the stereoscopic AR system during in-vivo procedures. Major internal structures could be easily identified. The system exhibited unobservable latency with acceptable image-to-video registration accuracy. As exhibited by these results a stereoscopic AR system according to the present disclosure provides new capabilities with respect to introducing new visual cues and enhancing visualization of the surgical anatomy, thereby improving the precision of, and expanding the capacity of, minimally invasive laparoscopic surgeries.

The collection of the following major features makes embodiments according to the present disclosure novel compared to existing systems:

1) Focus on creating composite multi modal images of deformable and moving surgical anatomy.

2) Tracking of imaging devices for registration of endoscopic video and intra-operative tomographic images.

3) Methods that address sterilization issues and produce a clinical system capable of OR use.

4) Methods for creating 3D tomographic data from primarily 2D intra-operative modalities (for example, ultrasound).

5) Methods for reconstructing organ surfaces from endoscopic video images.

6) Methods for registering intra- or pre-operative 3D tomographic images with laparoscopic video through high-speed surface-to-surface registration.

7) Methods for registering pre-operative 3D tomographic images with laparoscopic video through high-speed volume-to-volume registration.

8) Methods for registering pre-operative 3D tomographic images with laparoscopic video through high-speed feature-based registration.

9) Methods for creating a real-time image augmentation system with low latency.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 21 illustrates an exemplary velocity profile of the DC motor during image capture, according to certain embodiments.

DETAILED DESCRIPTION

Figure 1:
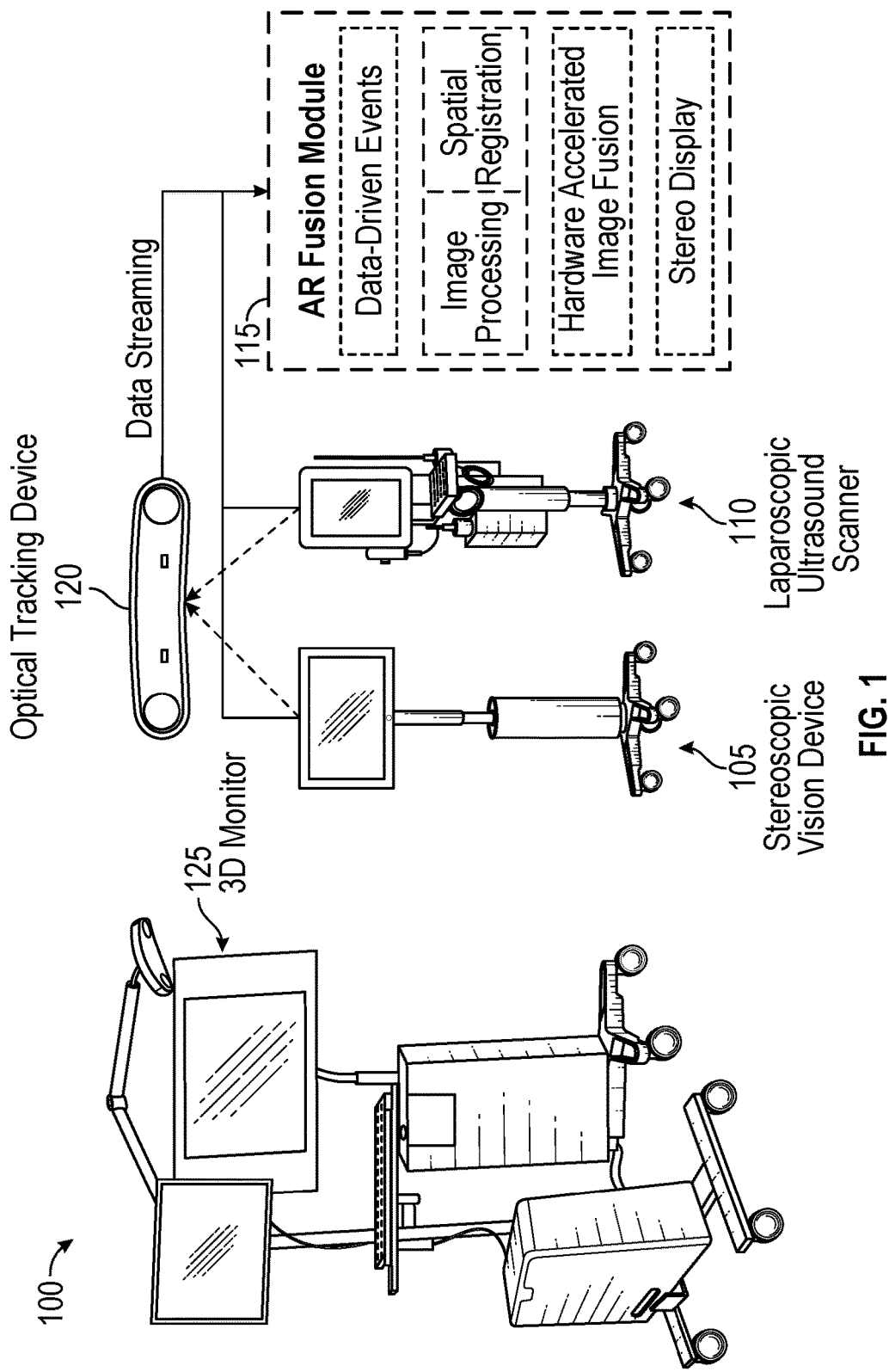
FIG. 1 illustrates a non-limiting exemplary stereoscopic AR system and a block diagram including procession circuitry components corresponding to an AR fusion module, according to certain embodiments.

Referring now to the drawings, wherein like reference numerals designate identical or corresponding parts throughout the several views.

FIG. 1 illustrates an exemplary stereoscopic AR system and a block diagram AR fusion module with major processing circuitry components for generating composite image data, according to certain embodiments. Stereoscopic AR system 100 includes two imaging devices: a stereoscopic vision device 105 and a laparoscopic ultrasound scanner 110. In certain embodiments, the stereoscopic vision device 105 may be a VSII by Visionsense Corp. with a 5-mm laparoscope (called 3D laparoscope henceforth), and the ultrasound scanner device 110 may be a flex Focus 700 by BK Medical with a 10-mm laparoscopic transducer. In certain embodiments, the 3D laparoscope may be a zero-degree scope with 70-degree field of view. The 3D laparoscope may have a fixed focal length of 2.95 cm. The 3D laparoscope provides an integrated light source and automatic white balance, both of which simplify the use in an OR setting. The LUS transducer may have an operating frequency range of 5 MHz-10 MHz with a maximum scan depth of 13 cm. The LUS scanner system is capable of gray-scale B-mode and color Doppler mode scanning. Both devices are FDA cleared for clinical use. To make the stereoscopic AR system 100 portable for OR use, all the components were assembled on a rolling cart, as shown in FIG. 1.

In the exemplary stereoscopic AR system 100, the stereoscopic video and LUS images are streamed to a stereoscopic AR fusion module 115 over high-speed Ethernet from the 3D stereoscopic vision system and the LUS scanner. An optical tracking device 120 (e.g., Polaris by Northern Digital Inc.) is used to track the pose (location and orientation) of the 3D laparoscope and the LUS transducer. Utilizing the tracking data, the LUS images are overlaid onto the stereoscopic video in real time, creating two ultrasound-augmented video streams (one for the left eye and the other for the right) for stereoscopic visualization. These two video streams are displayed on a 3D monitor 125, and users can perceive 3D effect (stereopsis) by wearing passive polarized glasses.

The clinical success of the system described herein is facilitated by high-performing (20 frames/second or greater high-definition video), low-latency (100 ms or less) image composition methods. Various embodiments according to the present disclosure may include high-performance computing platforms such as graphics processor units (OPUs), multi-core processors, or field-programmable gate arrays (FPOSs) for efficient data processing. In certain embodiments, the stereoscopic AR fusion module 115 that generates the ultrasound-augmented video streams using the received LUS images, stereoscopic video and tracking data may be implemented on a 64-bit Windows 7 PC with an 8-core 3.2 GHz Intel CPU, 12 GB memory, and an NVidia Quadro 4000 graphics card. This implementation resulted in performance characteristics consistent with the above metrics for performance and latency, as will be discussed in later sections.

Figure 2:
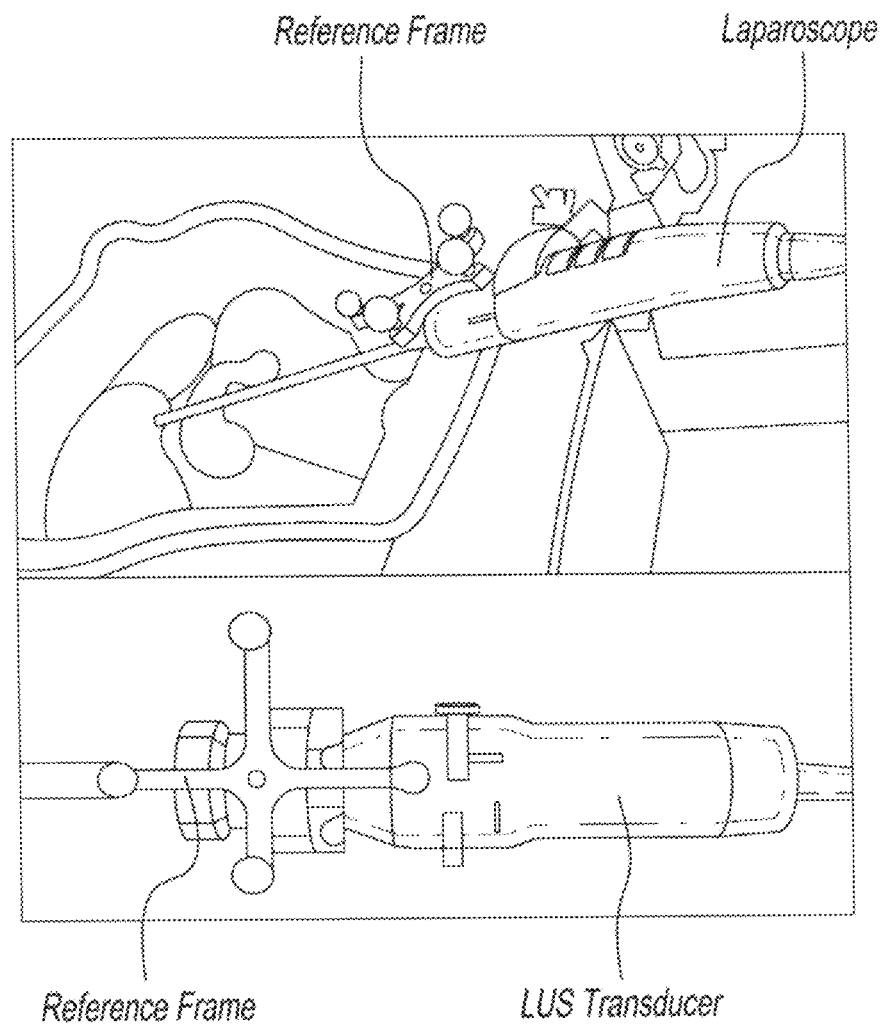
FIG. 2 illustrates non-limiting exemplary rigid mounts that can be sterilized and coupled with an imaging device in a reproducible manner and on which tracking sensors/markers can be attached at their pre-determined locations, according to certain embodiments.
Figure 3B:
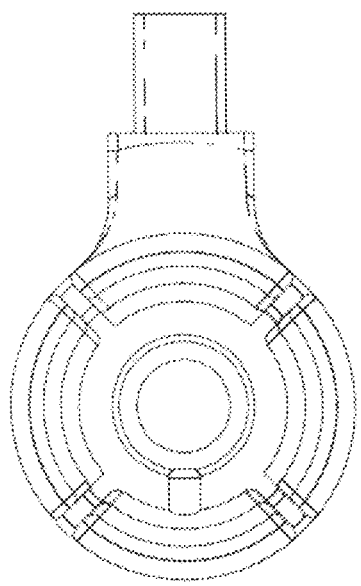
FIGS. 3A-3F illustrate various views of non-limiting exemplary fixtures for a 3D laparoscope and a LUS transducer, according to certain embodiments.
Figure 3C:
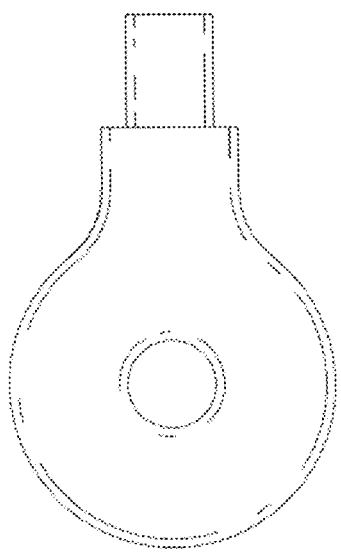
Figure 3A:
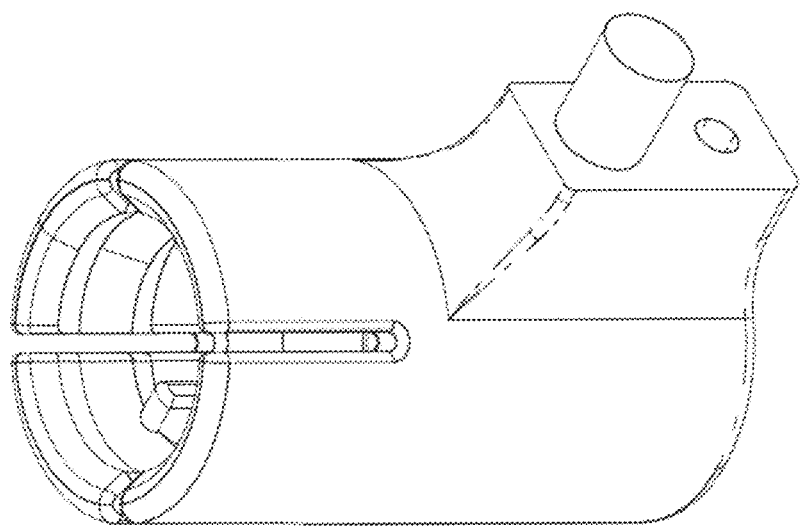
Figure 3E:
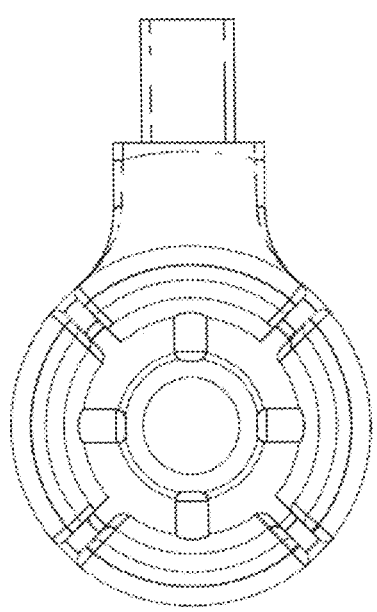
Figure 3F:
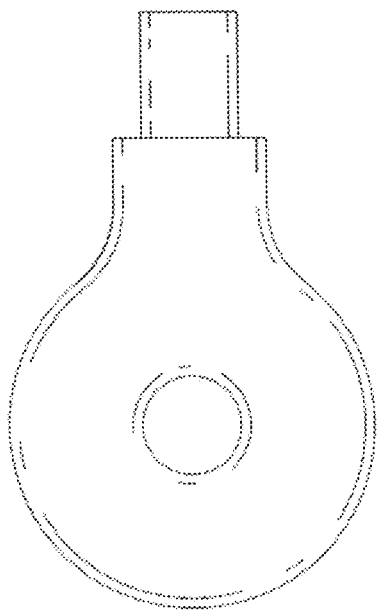
Figure 3D:
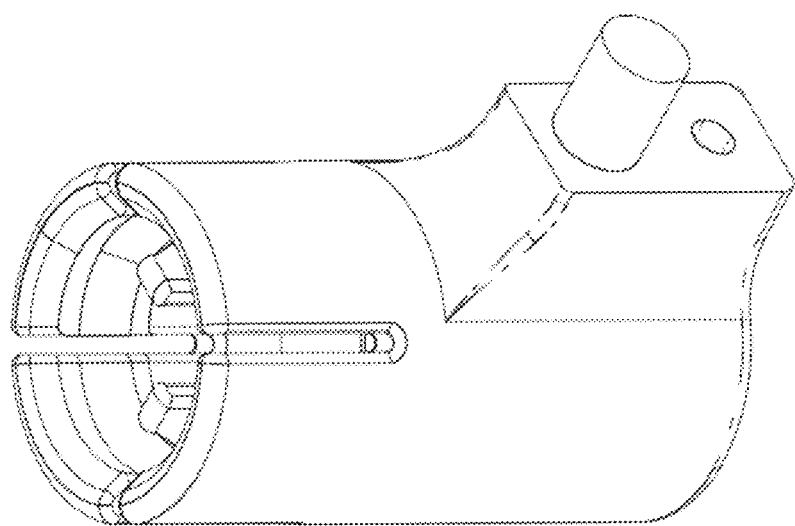

To track the 3D laparoscope and the LUS transducer, two reference frames with passive reflective spheres may be mounted onto their respective handles (see FIG. 2, where an exemplary 3D laparoscope is shown in the top image and an exemplary LUS transducer is shown in the bottom image). The rigid structure of the 3D laparoscope and the LUS transducer allows tracking them through the reference frames, whose pose with respect to the tracker is known in real-time.

An OR-friendly system design is important for clinical viability and routine OR use of the stereoscopic AR system 100. In particular, the ease of OR setup and system portability are two major aspects of OR compatibility.

Because the 3D laparoscope and the LUS transducer must be sterilized before each OR use, the reference frames affixed on them (see FIG. 2) for tracking purposes must be disassembled and sterilized separately. The system calibration could be performed in the OR after reattaching the reference frames; however, doing so would consume expensive OR time and require an extra technician as part of the surgical team.

Calibration of the imaging devices is a prerequisite for creating composite multi-modality images. Calibration establishes (1) the spatial relationship between the actual image (ensemble of pixels or voxels) with respect to the geometry of the imaging device, and (2) the relative spatial position and orientation between the two (or more) imaging devices. Calibration often requires attaching a set of tracking sensors/markers on the imaging devices and the calibration parameters are sensitive to their location and arrangement. As discussed previously, the need to sterilize imaging devices before a surgery means that the tracking sensors/markers must be removed before sterilization and reattached in the OR prior to surgery. This also necessitates repeating a lengthy calibration process, which is not practical in conjunction with a live surgical procedure.

A novel aspect of the present disclosure is rigid custom mounts (as shown in FIGS. 3A-3F) that can be sterilized and coupled with imaging devices in a reproducible manner and on which tracking sensors/markers can be attached at their pre-determined locations. As non-limiting examples of such custom mounts, FIGS. 3A-3C correspond to perspective, top, and bottom views of the laparoscope mount; and FIGS. 3D-3F correspond to perspective, top, and bottom views of the LUS transducer mount. The reproducible mounting feature of the present disclosure makes the combining of multimodality images practical and suitable for routine surgical use. Specifically, to be able to reuse laboratory calibration results in the OR and thus minimize OR setup time, the reference frames should be affixed on the transducers in exactly the same position as they were before disassembly. For this, mechanical fixtures such as those in FIGS. 3A-3F may be affixed on the 3D laparoscope and the LUS transducer, and these fixtures served as mounts for reference frames needed for optical tracking. This strategy maintains a fixed geometric relationship between the reference frames and the imaging devices before and after sterilization.

The fixture for the 3D laparoscope (see FIGS. 3A-3C) was printed on a 3D printer (e.g., Objet500 Connex by Stratasys Ltd.) using a material that can withstand a standard sterilization process. The fixture for the LUS transducer (see FIG. 3E-3F) was made using aluminum. The fixtures can be easily mounted on their respective corresponding devices in a unique way.

The image-to-video registration accuracy is critical from the standpoint of surgical safety when implementing the stereoscopic AR system 100. The optical tracking device 120 is rated to have sub-millimeter (i.e., negligible) tracking error. The main determinants of the accuracy in the developed system therefore come from how accurately the imaging parameters of the two imaging devices (focal length, lens distortion and pixel size for the 3D laparoscope; scan depth and pixel size for the LUS transducer) are estimated during system calibration.

Various techniques, such as Zhang's method [3], may be used for calibrating the 3D laparoscope and various techniques, such as the method proposed by Yaniv et al. [4], may be used for calibrating the LUS transducer. To obtain stable and accurate tracking data, the optical tracking device 120 may be mounted on a stationary tripod and the 3D laparoscope and the LUS transducer may be held by a clamp to avoid hand tremor. Calibrations were performed in approximately 30 minutes in a laboratory setup consistent with the exemplary stereoscopic AR system 100 but may be performed for any suitable period.

In the exemplary stereoscopic AR system 100, the use of LUS eliminates any risk of radiation exposure and provides real-time imaging with multiple scanning modes (e.g., B-mode and color Doppler mode). The developed system also facilitates interpretation of LUS images. In conventional practice, LUS images are displayed on a separate display monitor and are thus visually disconnected from the live laparoscopic video. This separate presentation requires that the surgeons mentally register the two types of images.

This task is difficult to perform in general, and is especially difficult in the stressful environment of the OR. It is also variable with operator expertise and prone to error. In contrast to conventional techniques, the stereoscopic AR system 100 presents the LUS images in correct reference to the laparoscopic camera view in real time on the 3D monitor, obviating the need for mental image integration, eliminating associated errors, and potentially improving surgical efficiency.

Potential applications for stereoscopic AR visualization in accordance with the present disclosure include laparoscopic biliary surgery and partial organ resection procedures. In biliary surgery, this enhanced visualization will accurately identify the bile duct and vascular anatomy in real-time. If used as a training tool, resident identification of the common bile duct-cystic duct junction and vascular anatomy during laparoscopic cholecystectomy could become a standard of care by replacing other current techniques such as intraoperative cholangiogram and indocyanine green injection. In children, laparoscopic choledochal cyst excision and biliary reconstruction would be significantly enhanced by using stereoscopic AR because the variation and complexity of this condition is substantial. In these children, large dilated common bile ducts may obscure the portal vein due to both size and inflammation such that blind dissection behind the cyst results in major hemorrhage. With 3D AR visualization in subtotal organ resection procedures for tumors, identification of the tumor relative to normal parenchyma such as in the pancreas and kidney, will allow rapid identification of the tumor (in the absence of palpation or direct visualization when sub-parenchymal) as well as proximity of splenic vein/artery and renal vessels, pelvic calyces and ureter. These early potential applications make the visualization technology developed here equally applicable to both ablative and reconstructive procedures.

Next, exemplary processing for generating ultrasound-augmented video streams using the received LUS images, stereoscopic video and tracking data will be discussed in further detail with reference to FIG. 4. The following discussion assumes calibration of the imaging devices has been performed.

Figure 4:
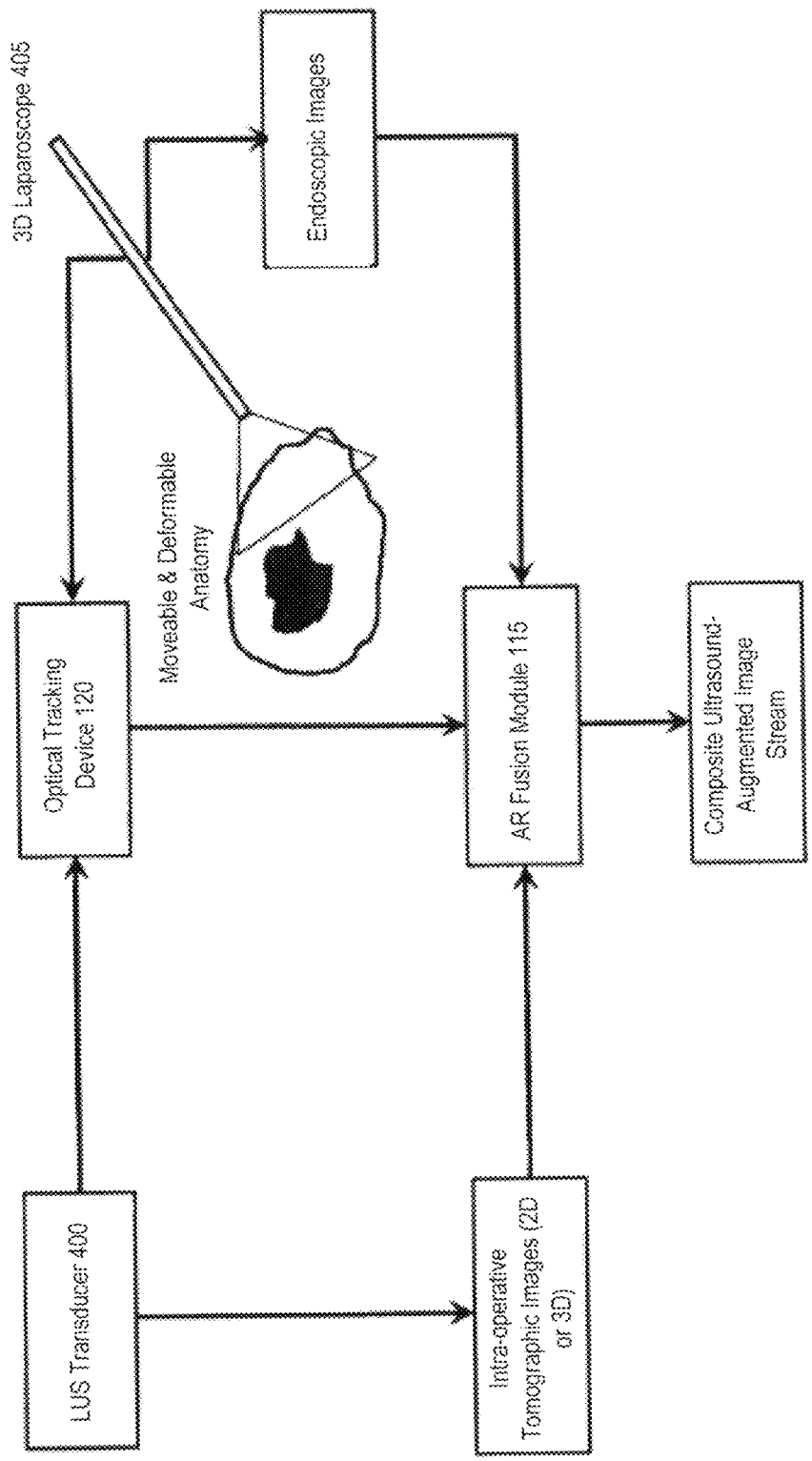
FIG. 4 is a non-limiting exemplary schematic flow diagram illustrating a method of creating composite images using tracked imaging devices, according to certain embodiments.

FIG. 4 includes a LUS transducer 400 and a 3D laparoscope 405, which may be included in the laparoscopic ultrasound scanner 110 and the stereoscopic vision device 105, respectively.

Most soft-tissue organs, especially those found in the thorax and the abdomen, are highly deformable. These organs deform and move because of factors such as respiration, heart rhythm, and gravity. During surgery, they also deform and move because of insufflation and surgical maneuvers, among other factors. It is critical when creating accurate composite images to ensure that the images being merged are of the anatomy in the same spatial state and pose. If the images are acquired simultaneously, this condition is easily met. If that is not the case, special methods that model soft-tissue deformation are needed to account for different spatial states and poses of the anatomy.

When the tomographic images are acquired intra-operatively together with endoscopic video (e.g., the intra-operative tomographic image data output by the LUS transducer 400 and the endoscopic image data output by the 3D laparoscope 405), the registration between the two types of images can be achieved by tracking the two imaging devices in the 3D space. Tracking in the stereoscopic AR system 100 is performed by the optical tracking device 120. Examples of tracking techniques that may be implemented by the optical tracking device 120 include but are not limited to optical, electromagnetic, acoustic, motion sensing, and mechanical arms. It should be noted that an important distinction of the present disclosure is the combination of pre-operative and intra-operative images (in addition to multiple modality intra-operative images), which is not available in conventional systems.

Another aspect of the present disclosure is reconstruction of intra-operative volumetric images from a set of planer (2D) intra-operative images if the intra-operative tomographic imaging system does not natively produce volumetric images. Because of the availability of spatial tracking data from the optical tracking device 120 in stereoscopic AR system 100, the 3D location and orientation of each planar image is known. Using methods such as "3D Ultrasound using Stradwin 4.7" developed at the University of Cambridge, tracked images can be combined to form a volumetric image. Furthermore, a volumetric image set can be updated by replacing the oldest planar image with the latest one, and repeating this procedure for each incoming image frame. The resulting 3D intra-operative tomographic images can be combined with endoscopic video in an identical fashion, as shown in FIG. 4. Furthermore, the volumetric image can be reformatted as any planar section (not necessarily aligning with the original acquisition planes) or as a volume rendered scene or as a projection image such as an x-ray. Alternatively, anatomic structures of interest can be segmented in volumetric intra-operative tomographic images. Any of these representations of the 3D intra-operative tomographic data can then be fused with the endoscopic video data in real time to generate the composite ultrasound-augmented image stream output. Additional detailed features related to forming volumetric images using 2D tomographic images will be discussed later at least with respect to FIGS. 13 through 21.

Figure 5:
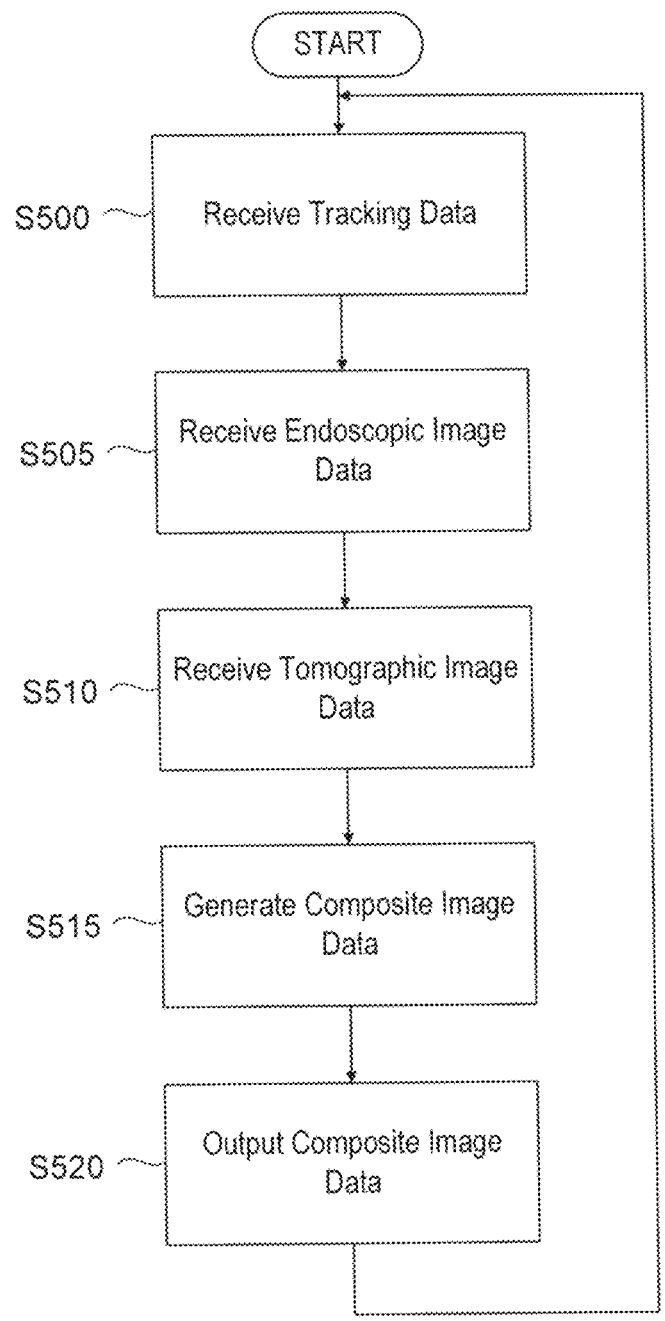
FIG. 5 illustrates a non-limiting exemplary flowchart corresponding to the generation of composite ultrasound-augmented image stream data, according to certain embodiments.

Next, FIG. 5 illustrates a non-limiting exemplary flowchart corresponding to the generation of composite ultrasound-augmented image stream data, according to certain embodiments. Individual imaging devices and a tracking system provide the input data streams. In this non-limiting example, the generation of the composite image is performed by specialized and efficient processing of input data streams by the AR fusion module 115 in the stereoscopic AR system 100.

At step S500, tracking data corresponding to both the 3D laparoscope and the LUS transducer is received by the AR fusion module 115 from the optical tracking device 120. As discussed previously, the tracking data may be applied for combining intra-operative images output by the respective imaging devices, and the composite image data can be generated by a combination of the respective imaging device outputs since the spatial orientation of each device is known to the AR fusion module 115.

At step S505, the AR fusion module 115 receives endoscopic image data from the 3D laparoscope 405.

At step S510, the AR fusion module 115 receives tomographic image data from the LUS transducer 400. As mentioned previously, the tomographic image data generated by the LUS transducer 400 and received by the AR fusion module 115 at step S510 may be 2D or 3D. If the tomographic image data is 2D, processing described herein may be performed for generating volumetric images corresponding to the 2D image data.

At step S515, the AR fusion module 115 generates composite ultrasound-augmented image data based on the received tracking data, endoscopic image data, and tomographic image data. For example, the AR fusion module 115 performs processing at step S515 for overlaying the LUS images onto the stereoscopic video in real time (utilizing the tracking data), creating two ultrasound-augmented video streams (one for the left eye and the other for the right) for stereoscopic visualization.

At step S520, the AR fusion module 115 outputs the composite image data for display. As mentioned previously, the composite image data may be output in two video streams that may be displayed on a 3D monitor such that users can perceive a 3D effect (stereopsis) by wearing passive polarized glasses.

Figures 6A, 6B:
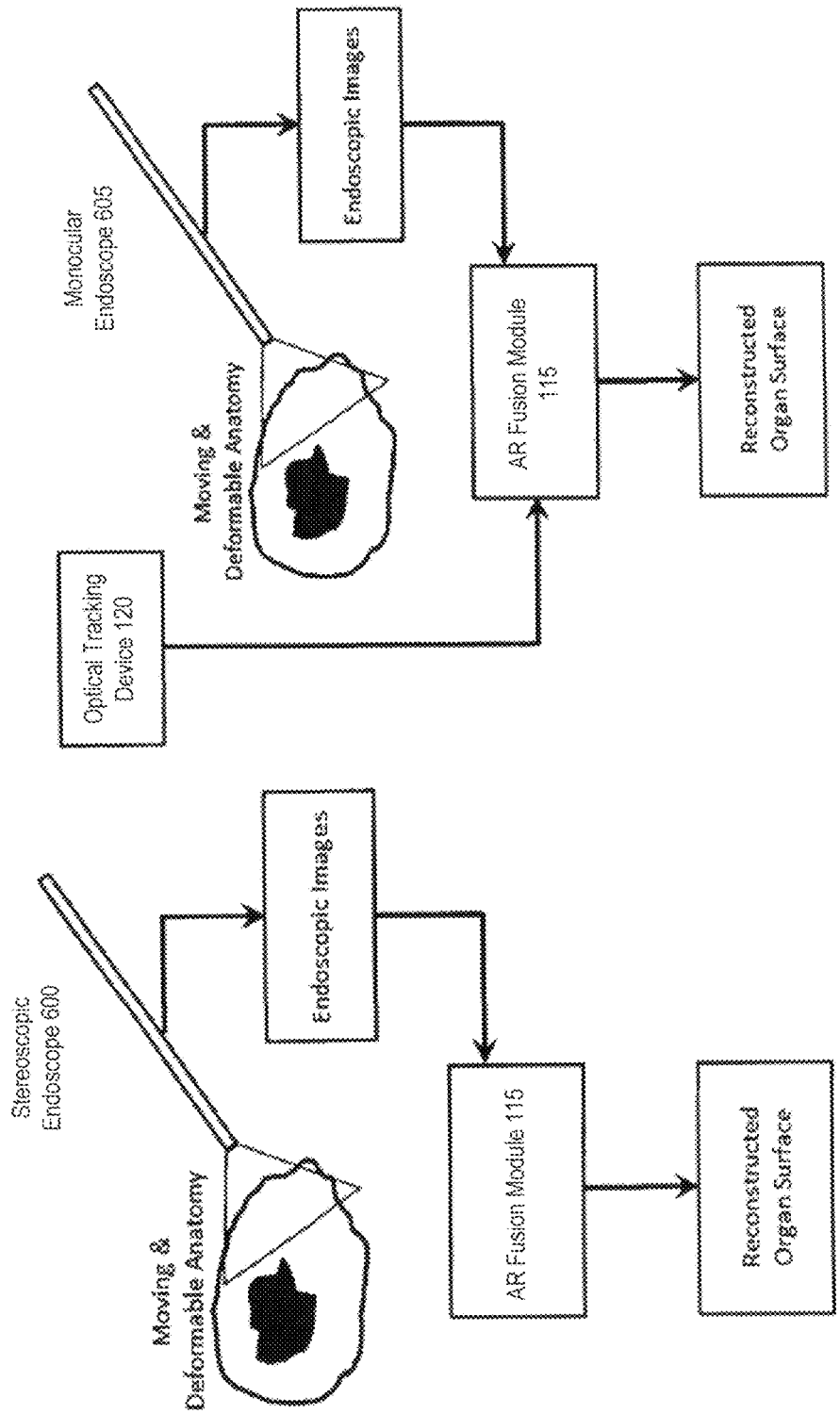
FIGS. 6A and 6B illustrate two non-limiting exemplary schemes of reconstructing organ surfaces using a stereoscopic and a monocular endoscope, respectively, according to certain embodiments.

Next, FIGS. 6A and 6B illustrate exemplary flow diagrams demonstrating two schemes of reconstructing organ surfaces using a monocular and a stereoscopic endoscope, respectively, according to certain embodiments. Processing related to generating reconstructed organ surface image data is illustrated in FIGS. 6A and 6B as being performed by processing circuitry included in the AR fusion module 115 of the stereoscopic AR system 100. Alternatively, the surface reconstruction module illustrated in FIGS. 6A and 6B may be implemented as a dedicated processing circuit included in other external devices connected in a wired or wireless network.

Stereoscopic endoscopes, by their very design, provide a pair of well-defined and fixed perspectives. Therefore, organ surfaces can be reconstructed without needing a tracking device (FIG. 6A). In other embodiments, multiple perspectives can be generated from sequential images of a spatially tracked monocular endoscope (FIG. 6B). These multiple perspectives can then be used to reconstruct the organ surface.

Figure 7:
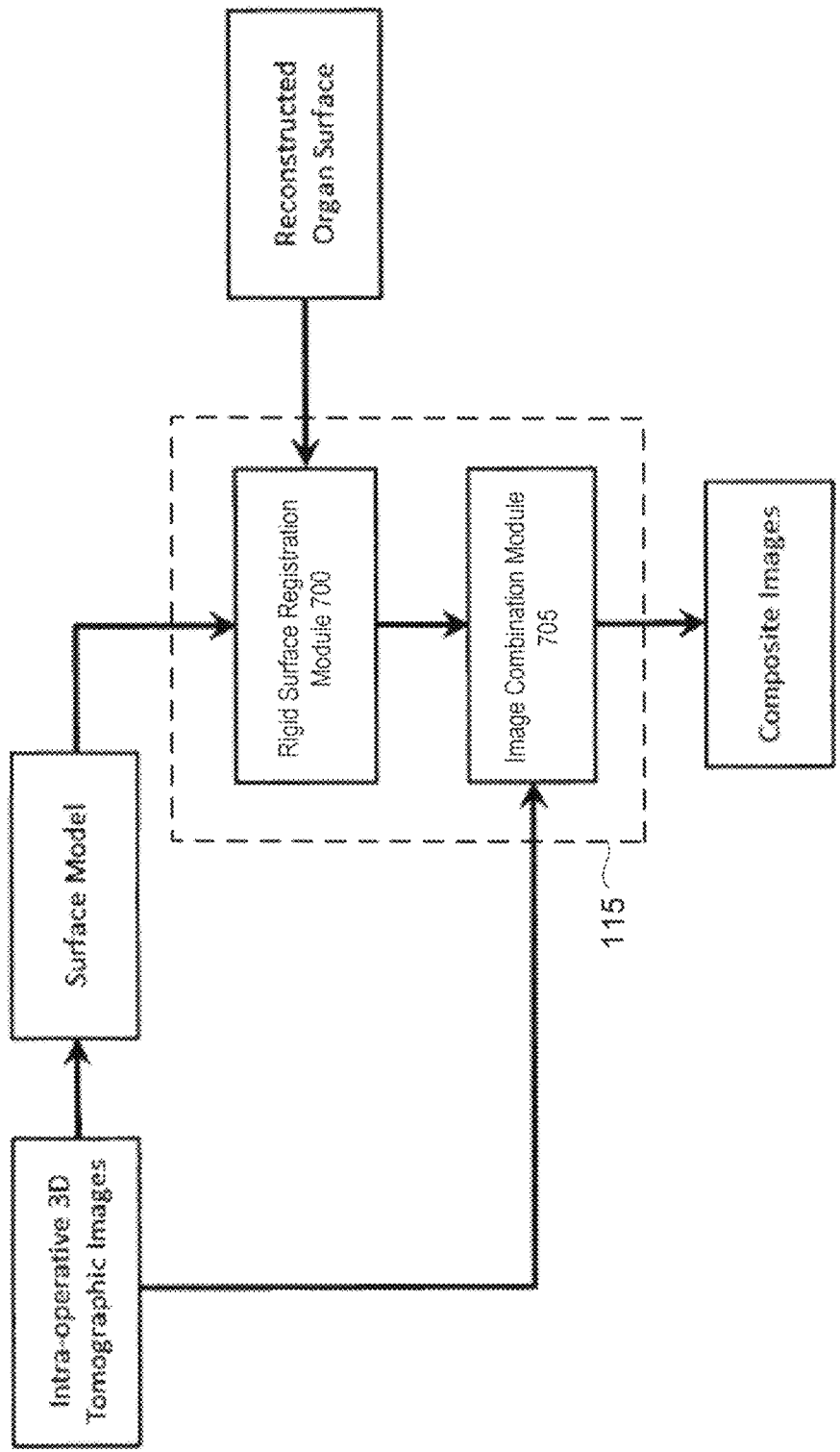
FIG. 7 is a non-limiting exemplary schematic flow diagram illustrating a method of creating composite stereoscopic images using rigid registration of surface model derived from intra-operative tomographic images and a surface model reconstructed from the endoscopic images, according to certain embodiments.

Next, FIG. 7 is a schematic drawing illustrating an exemplary method of creating composite stereoscopic images using rigid registration of a surface model derived from intra-operative tomographic images and a surface model reconstructed from the endoscopic images as described in FIGS. 6A and 6B, according to certain embodiments. FIG. 7 includes a rigid surface registration module 700 and an image combination module 705, which may each be implemented by processing circuitry included in the AR fusion module 115 of stereoscopic AR system 100. Alternatively, the modules illustrated in FIG. 7 may be implemented as dedicated processing circuits included in other external devices connected in a wired or wireless network.

The intra-operative volumetric tomographic image, if acquired natively in real time, for example, from a 3D ultrasound device with 2D matrix of transducer elements, can be registered with endoscopic video through surface registration (as shown in FIG. 7). A rigid registration between the organ surfaces segmented from the intra-operative 3D tomographic image and reconstructed from endoscopic video is sufficient to align the two modalities before creating composite images because the two modalities provides live images of the surgical anatomy in this embodiment.

Figure 8:
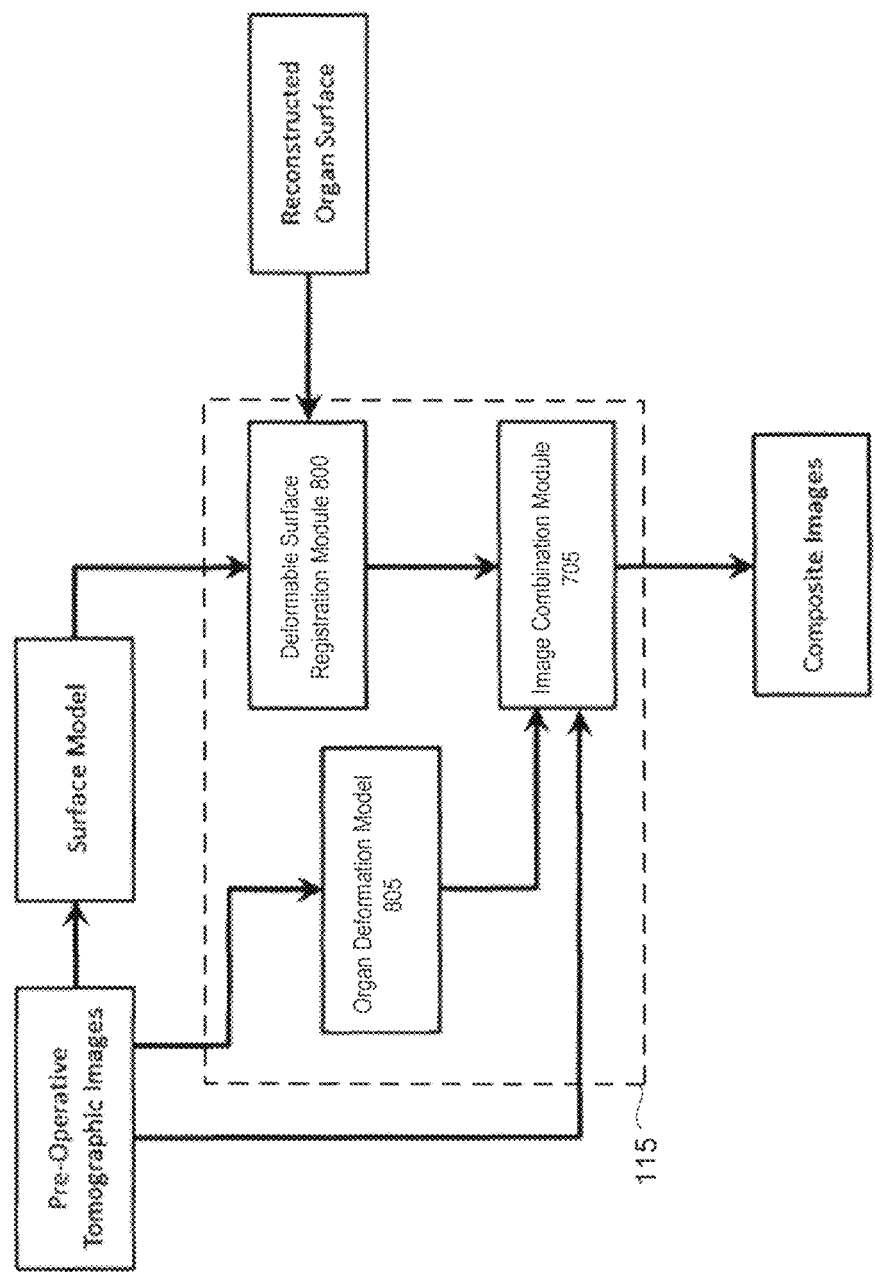
FIG. 8 is a non-limiting exemplary schematic flow diagram illustrating a method of creating composite stereoscopic images through deformable registration of surface models derived from pre-operative tomographic images and surface models reconstructed from endoscopic images, and using an organ deformation model, according to certain embodiments.

Next, FIG. 8 is a schematic drawing illustrating an exemplary method of creating composite stereoscopic images through deformable registration of a surface model derived from pre-operative tomographic images and a surface model reconstructed from the endoscopic images, and using an organ deformation model, according to certain embodiments. FIG. 8 includes a deformable surface registration module 800, an organ deformation model 805, and the image combination module 705, which may each be implemented by processing circuitry included in the AR fusion module 115 of stereoscopic AR system 100. Alternatively, the modules illustrated in FIG. 8 may be implemented as dedicated processing circuits included in other external devices connected in a wired or wireless network.

Real-time deformable registration of pre-operative volumetric tomographic images, examples of which include CT and MR imaging scans, with endoscopic video is also a feature of the present disclosure. As shown in FIG. 8, the pre-operative tomographic images may be received as inputs into the deformable surface registration module 800, the organ deformation module 805, and the image combination module 705. A large non-rigid misalignment is generally expected between the anatomy that appears in pre-operative tomographic images and the actual intra-operative anatomy, furthermore, it is expected to vary continuously during the surgery.

Processing according to the present disclosure solves the deformable image registration task by the following three methods. Various embodiments of the present disclosure may include one or more of these registration approaches.

1) Organ surfaces (or surfaces patches) identified in pre-operative tomographic images are deformably registered with corresponding surfaces (or surface patches) obtained from either endoscopic video or intra-operative volumetric images using a deformable surface registration method implemented by the deformable surface registration module (as shown in FIG. 8). Exemplary methods that may be implemented by the deformable surface registration module include, for example, Iterative Closest Point (ICP). Other examples are described in "An algorithmic overview of surface registration techniques for medical imaging" (Med Image Anal. 2000 September; 4 (3): 201-17, Audette M A, Ferrie F P, Peters T M), herein incorporated by reference. The result of the registration is then propagated to the entire pre-operative tomographic volume using previously computed organ deformation models. Furthermore, the method is carried out several times a second through a high-speed implementation of the registration algorithm to provide up-to-date depiction of the dynamically changing surgical anatomy.

Figure 9:
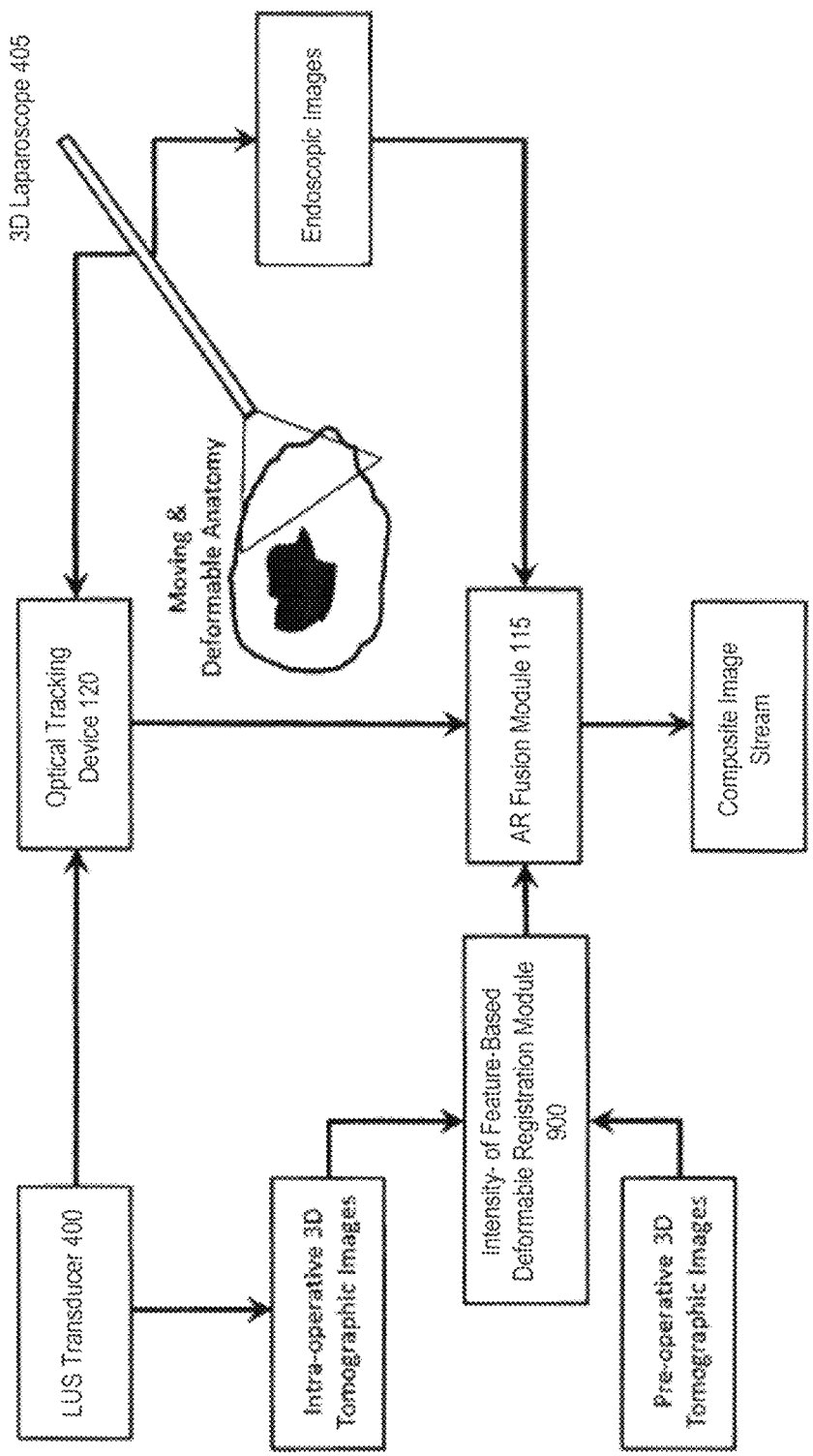
FIG. 9 is a schematic drawing illustrating a method of creating composite stereoscopic images using deformable image registration of pre- and intra-operative tomographic images, tracked imaging devices, and tracked endoscope, according to certain embodiments.

2) The pre-operative tomographic image volume is registered with intra-operative tomographic image volume using an intensity-based deformable image registration algorithm. For instance, the intensity-based deformable image registration algorithm maybe one of the algorithms described in "Automatic elastic image registration by interpolation of 3D rotations and translations from discrete rigid-body transformations" (Walimbe V, Shekhar R. Med Image Anal. 2006 December; 10(6):899-914. Epub 2006 Oct. 31) or "Nonrigid registration using free-form deformations: application to breast MR images" (Rueckert D, Sonoda L I, Hayes C, Hill D L, Leach M O, Hawkes D J. IEEE Trans Med Imaging. 1999 August; 18(8):712-21), both of which are incorporated herein by reference. The intensity-based deformable image registration algorithm may be implemented by an intensity- or feature-based deformable registration module 900, which may be implemented as processing circuitry within the AR fusion module 115 (as shown in FIG. 9). Furthermore, the method is carried out several times a second through a high-speed implementation of the registration algorithm to provide up-to-date depiction of the dynamically changing surgical anatomy.

3) Using suitable methods, anatomic structures in the preoperative tomographic image volume are segmented. The same structures are obtained in the intraoperative tomographic image volume either through image segmentation or as part of the imaging process (for example, the Doppler mode of ultrasound identifies blood vessels inherently). An existing feature-based registration method is then applied to register pre-operative tomographic images with intra-operative tomographic image volume (as shown in FIG. 9). Furthermore, the registration is carried out several times a second through a high-speed implementation to provide up-to-date depiction of the dynamically changing surgical anatomy.

Once the pre-operative tomographic images are registered with intra-operative tomographic images, a triple modality combination (pre-operative tomographic data, intra-operative tomographic data, and intraoperative endoscopic video) can be performed in one or more embodiments of the present disclosure. In other embodiments, the intra-operative tomographic data can be skipped in favor of a dual modality combination (pre-operative tomographic data and intra-operative endoscopic video).

Any reference to tomographic images described herein may reference any one or combination of images obtained by computed tomography (CT), single-photon emission computed tomography (SPECT), magnetic resonance imaging (MRI), positron emission tomography (PET), and Magnetic particle imaging (MPI), and ultrasound. The types of tomographic images are not limited to this list and may be any suitable tomographic image obtained by any suitable tomographic imaging technique.

EXPERIMENTAL RESULTS

A series of experiments were conducted using a developed stereoscopic AR system consistent with above-described embodiments of the present disclosure. The system latency and image-to-video registration accuracy were measured in a well-controlled laboratory setting. To further evaluate the system performance, a phantom study and two animal studies were performed.

System Evaluation

Low system latency and high image-to-video registration accuracy are critical for a successful clinical AR system. Poor latency or a notable lag between the movement of the imaging devices and the corresponding pictures on the display monitor will not be clinically acceptable. Likewise, poor image-to-video registration accuracy resulting in misaligned structures in the AR output will render the system unhelpful.

The system latency of the stereoscopic AR system (including hardware components described above for certain embodiments) was measured using the well-accepted method of imaging a high-resolution (millisecond) digital clock. The difference between the actual (clock) time and the time seen in the output image of the stereoscopic AR system determines the system latency. To account for all delays, the stereoscopic AR system was operated in the full-function mode with simultaneous LUS imaging. Several measurements were made to arrive at a mean value.

Figure 10:
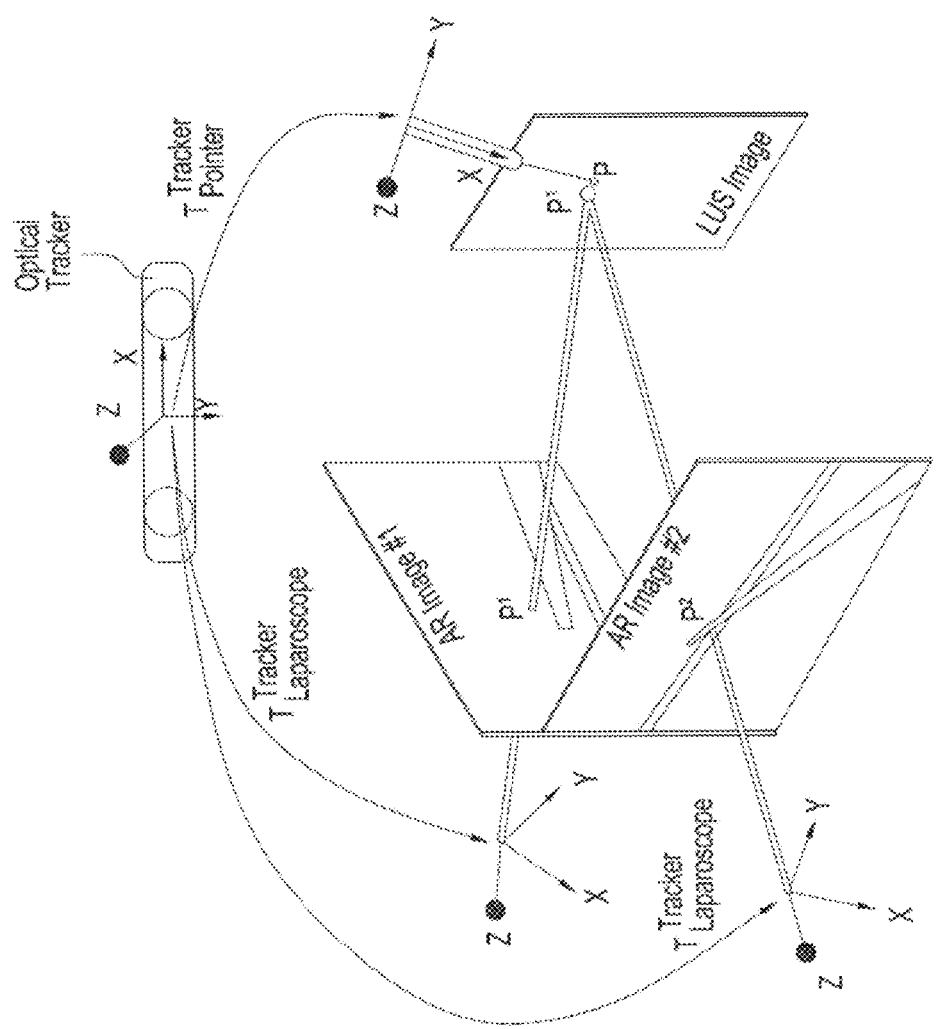
FIG. 10 is a non-limiting exemplary diagram illustrating a determination of target registration error for a stereoscopic AR system, according to certain embodiments.

The image-to-video registration accuracy depends on 1) the calibration accuracy of the 3D laparoscope, 2) the calibration accuracy of the LUS transducer, and 3) the stereoscopic AR visualization accuracy. The target registration error (TRE) metric was used to measure these accuracies. Given a 3D point, the TRE is defined as the 3D distance from its actual (reference) location to the computed location of the point. FIG. 10 depicts the procedure of calculating TRE in this experiment. A tracked pointer, held by a clamp, with its tip merged in a water tank was imaged using the tracked LUS (held by another clamp). Two frames of stereoscopic AR video were then produced by aiming the tracked 3D laparoscope at the pointer tip from two different angles. The tip of the pointer provided the reference location (denoted as P). Its estimated location (denoted as P') was calculated through triangulation [5] using the two AR frames. Finally, the TRE was computed as the 3D distance from P to P'.

Phantom Study

An intraoperative abdominal ultrasound phantom (IOUS-FAN, Kyoto Kagaku Co. Ltd., Kyoto, Japan), created specifically for laparoscopic applications, was used to demonstrate the stereoscopic AR system capability. The phantom includes realistic models of the liver, spleen, kidneys, pancreas, biliary tract, and detailed vascular structures, and simulated lesions such as biliary stones and cysts, solid tumors in liver, pancreas, spleen and kidneys.

Animal Study

All animal procedures were approved by the Institutional Animal Care and Use Committee (IACUC) and the animals were treated in accordance with the PHS Policy on Humane Care and Use of Laboratory Animals, the National Institutes of Health Guide for the Care and Use of Laboratory Animals, and the Animal Welfare Act. After successful anesthesia and intubation, a 40-kg female Yorkshire swine was placed in left decubitus position. Two trocars were placed—midline mid abdomen (12 mm, for instruments and LUS transducer) and right anterior axillary line in the lower abdomen (5 mm for 3D laparoscopic camera). Additionally, a hand port was placed in the midline lower abdomen to provide direct access for enhanced tissue manipulation. Carbon dioxide pneumoperitoneum at a pressure of 10 mmHg was created. After registration of the optical markers between the 3D laparoscopic camera and the LUS transducer, real-time tracking and stereoscopic AR visualization was started. Right kidney, liver, and biliary structures were examined with the real-time LUS images superimposed on the 3D laparoscopic video to provide internal anatomical details of the organs. The second study, also on a 40-kg female Yorkshire swine, followed the same procedure.

Results

The system latency was measured to be 144±19 ms. This result includes the native latencies of the constituent imaging systems and those of data streaming and stereoscopic AR visualization computation pipeline. The calibration accuracy of the LUS transducer, the calibration accuracy of the 3D laparoscope, and the overall stereoscopic AR visualization accuracy were 1.08±0.18 mm, 0.93±0.18 mm (left-eye channel) and 0.93±0.19 mm (right-eye channel), 3.34±0.59 mm (left-eye channel) and 2.76±0.68 mm (right-eye channel), respectively.

Phantom Study Results

Figure 11:
FIG. 11 illustrates three exemplary stereoscopic AR video snapshots (left-eye channel) recorded during the phantom study utilizing a stereoscopic AR video system according to certain embodiments, wherein each row has the original 3D laparoscopic camera image (left column), the original LUS image (middle column), and the stereoscopic AR image generated by the system (right column)

FIG. 11 shows two representative frames of the left-eye channel of the stereoscopic AR video generated using a system consistent with the exemplary stereoscopic AR system 100. The laparoscopic video, augmented with LUS images, reveal the internal structures in the liver. The first row has an LUS cross-section of a gall bladder overlaid on the laparoscopic camera view (composite image 1100). In the same manner, the second row has the intrahepatic vessels overlaid with LUS image data of a simulated tumor within the liver (composite image 1105), and the third row shows the common bile duct (composite image 1110).

Animal Study Results

Figure 12:
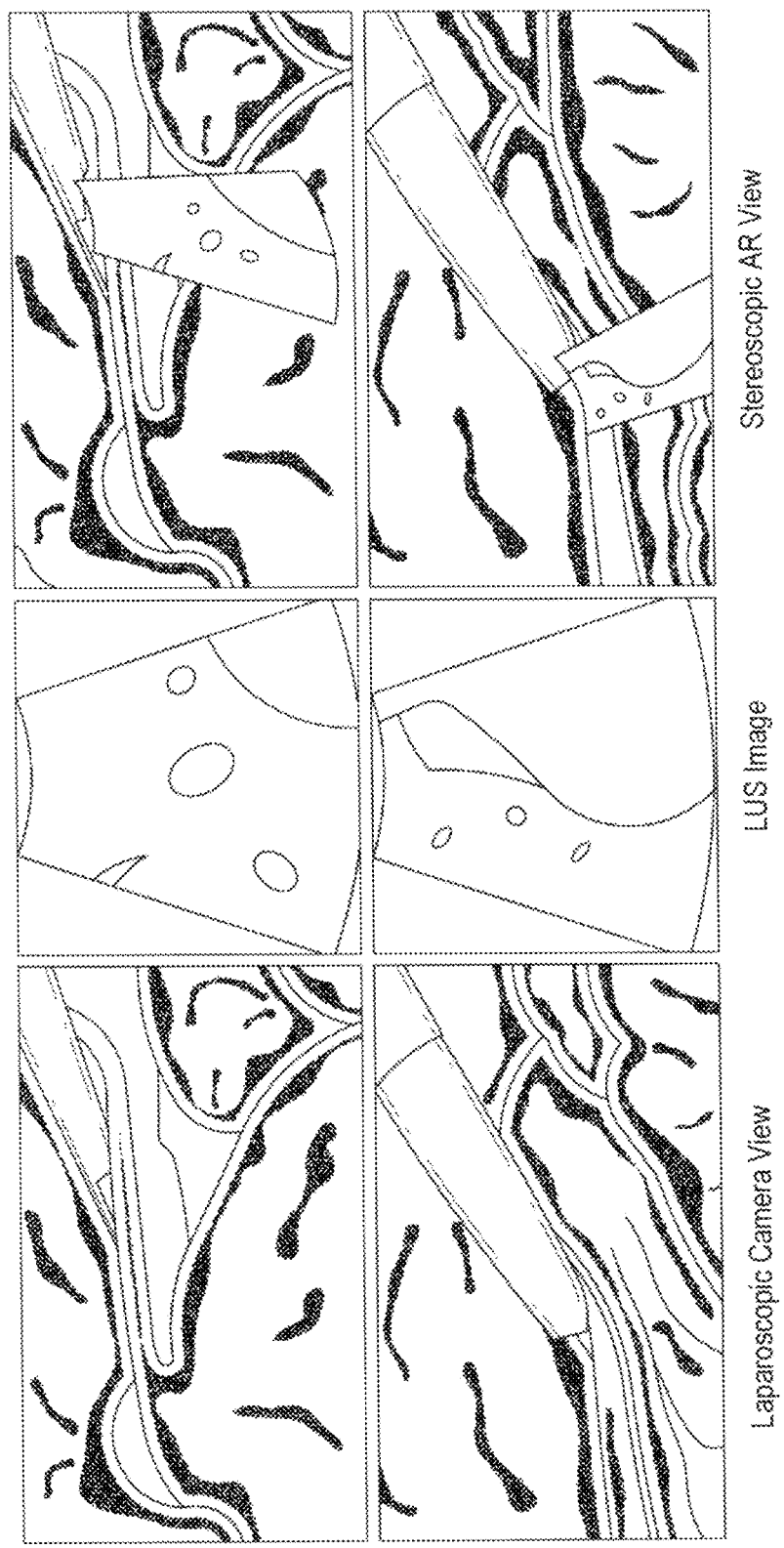
FIG. 12 illustrates two exemplary stereoscopic AR video snapshots (left-eye channel) recorded during an animal study using a stereoscopic AR video system according to certain embodiments, wherein each row has the original 3D laparoscopic camera image (left column), the original LUS image (middle column), and the stereoscopic AR image generated by our system (right column)

A stereoscopic AR system consistent with the embodiment of FIG. 1 was successfully used for visualization experiments in two swine. Subsurface anatomical structures along with vascular flow in the liver, kidney, and biliary system were clearly observed. The surgeons were able to identify the major branches of the right renal vasculature throughout the parenchyma of the kidney from the hilum to the renal cortex. The calyces were also able to be identified in relation to the visible renal capsule. Next, the liver was interrogated with good visibility of internal vasculature and major biliary structures. Even with rapid movements of the LUS transducer, the system latency was not noticeable to the naked eye. Visibility of the LUS image overlay was affected by the contrast of the background tissue. Darker tissues (renal parenchyma, liver) allowed for better visualization of the LUS overlay than lighter tissues (Gerota's fascia, bowel, peritoneum). The presence and use of the optical tracker was not seen to impede surgeon access or clinical workflow. Representative 2D image captures are shown in FIG. 12, including the 3D laparoscopic video images (left-eye channel), the LUS images, and the output stereoscopic AR video images (left-eye channel) recorded in the animal studies. The LUS images were overlaid onto the video images correctly and the internal structures beneath the liver were visualized clearly at their proper locations.

Next, embodiments of an AR system including a continuous hands-free volumetric ultrasonic scanning device implemented in an OR table will be described with reference to FIGS. 13 through 21. In certain embodiments according to the present disclosure, the output of an ultrasound imaging system consistent with embodiments described below may be utilized as an input for generating composite image data in the stereoscopic AR system 100.

Figure 13:
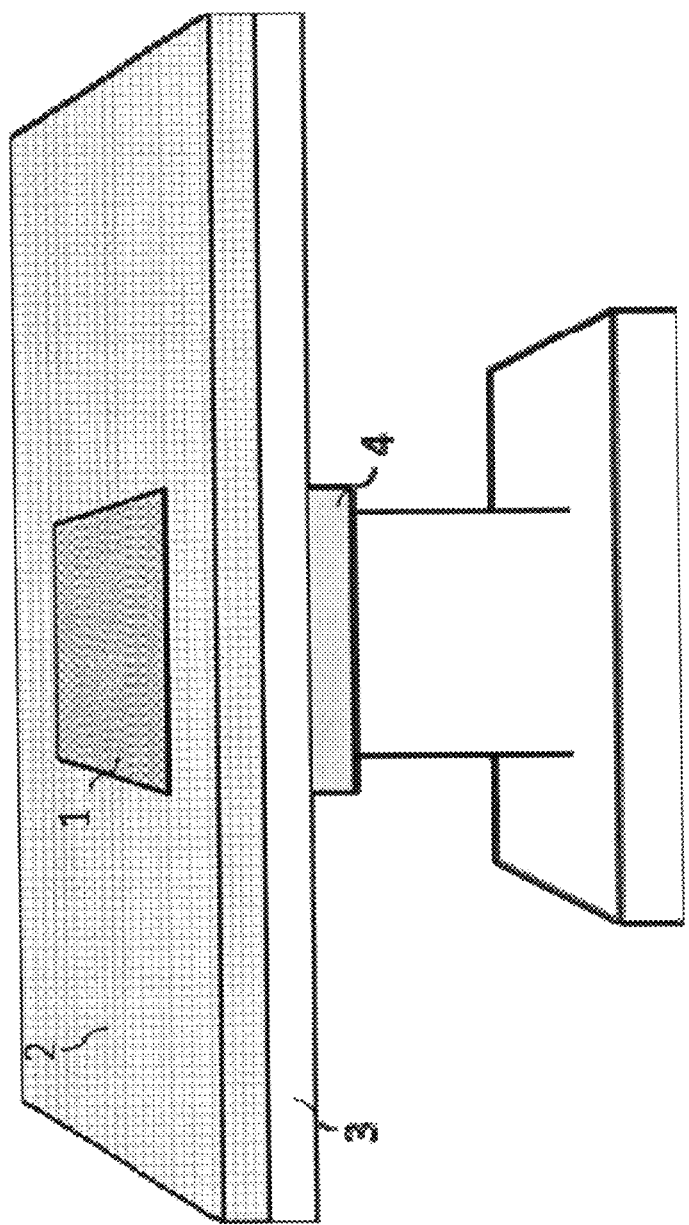
FIG. 13 illustrates an exemplary overview of an intraoperative 3D ultrasound acquisition system, according to certain embodiments.

First, FIG. 13 illustrates an exemplary overview of an intraoperative 3D ultrasound acquisition system, according to certain embodiments.

In ultrasound-guided procedures, continuous hands-free volumetric scanning of the patient lying on the OR table may be achieved in an implementation according to the exemplary embodiment of FIG. 13. Furthermore, a rendering of the 3D images from any desired viewing angle and/or in any desired format is available when utilizing this implementation. Because ultrasound is external to the body, in many cases, an additional port to introduce the laparoscopic ultrasound probe into the patient's body can be eliminated in this exemplary implementation. There is also no need for an extra hand to hold and operate the ultrasound probe.

In FIG. 13, an overview of the 3D ultrasound scanning system is presented. The 3D scanning module, also referred to hereinafter as SonoTable, has a soft, flexible, and acoustically transparent top surface part 1 to make contact with the patient's body. A standard OR table pad 2 surrounds the SonoTable module. A tabletop part 3 supports the top surface part 1 and the table pad 2. A container box 4 below the SonoTable unit includes imaging components and a motor assembly for capturing ultrasound image data. Although shown as a part of an OR table, the SonoTable module is capable of being moved from one OR to another. For example, the SonoTable Module may be adapted to be removable from the OR table such that it may be transported and fitted to other OR tables, or the entire table assembly may be wheeled to another OR.

Figure 14:
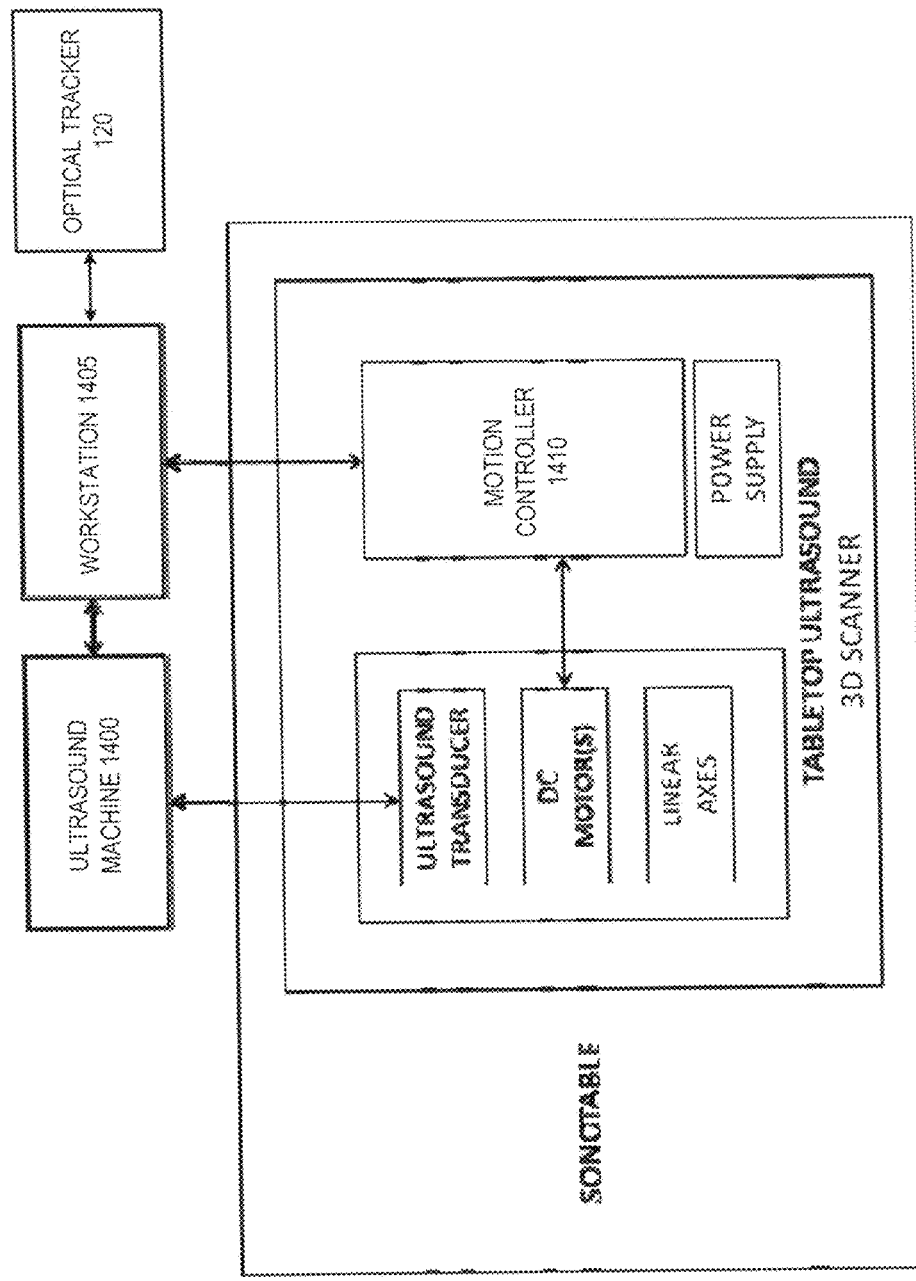
FIG. 14 illustrates an exemplary block diagram of an intraoperative 3D ultrasound acquisition system, according to certain embodiments.

Next, FIG. 14 illustrates an exemplary block diagram of an intraoperative 3D ultrasound acquisition system, according to certain embodiments.

Referring to FIG. 14, the exemplary 3D ultrasound scanning system of FIG. 14 includes an ultrasound machine 1400, the SonoTable unit, the optical tracker 120, and a workstation 1405 used for communication with the ultrasound machine 1400 and a motion controller 1410 and for performing image reconstruction and visualization tasks based on received image data and tracking data. In certain embodiments, the system of FIG. 14 may be implemented using a vision system such as VSII by Visionsense Corp., a 5-mm stereo laparoscope, an ultrasound machine such as flexFocus 700 by BK Medical with a robotic "drop-in" transducer, a mechanical ultrasound scanner, an optical tracker such as Polaris Vicra by Northern Digital, a drop-in transducer such as ProART by BK Medical, and a motion controller such as the DMC-41×3 by Galil Motion Control. The workstation 1405 includes one or more processors capable of executing instructions stored in a memory or received from a device on a network. The workstation 1405 optionally includes graphics cards supporting compute-intensive image processing. In one or more embodiments, the workstation may be implemented using a 64-bit Window 7 PC with an 8-core 3.2 GHz processor, 12 GB memory, and NVidia Quadro 4000 graphics card. The ultrasound machine 1400 supports image data streaming through high-speed Ethernet, RS-232, or other input/output communication interfaces. The motion controller 1410 allows single- or multi-axis scanning with the ability to set motor control parameters of position, velocity, acceleration, and deceleration. The tracked position of the transducer on the linear stage is acquired using a library provided by the manufacturer of the motion controller 1410. The optical tracker 120 and passive reflective markers on the dynamic reference frame (DRF) fixed to tracking targets may be used to track the 3D pose (location and orientation) of the stereoscopic laparoscope and the mechanical ultrasound scanner in real time. The workstation 1405 also performs volume reconstruction, image processing, volumetric rendering, image fusion, and stereoscopic visualization.

Device calibration is critical for accurately overlaying different types of images, such as in the image processing according to the present disclosure. For stereoscopic laparoscope calibration, a 9-by-6 checkerboard of alternating 5-mm black and white squares may be used. The size of the square may be selected to ensure that the entire checkerboard always lies within the field of view of the laparoscope at the recommended working distance. The transformation from the laparoscope to the DRF attached to it may be determined from the 3D coordinates defined by the four corners of the checkerboard pointed to by a tracked pointer. The intrinsic parameters of the laparoscopic camera may be estimated using, for example, Zhang's method [3].

For ultrasound calibration, the calibration phantom of PLUS5 may be used. For example, suture wires may be used to form three "N" shapes with known geometry related to the phantom. Because position tracking data and image data are not synchronized, the time difference between them may be recorded and taken into account in calibration. During calibration, the transducer is fixed at the starting position with the motor turned off. The nine intersecting points of the N-wires in the ultrasound frames continuously imaged at varying positions may be used for calibration.

Figure 15:
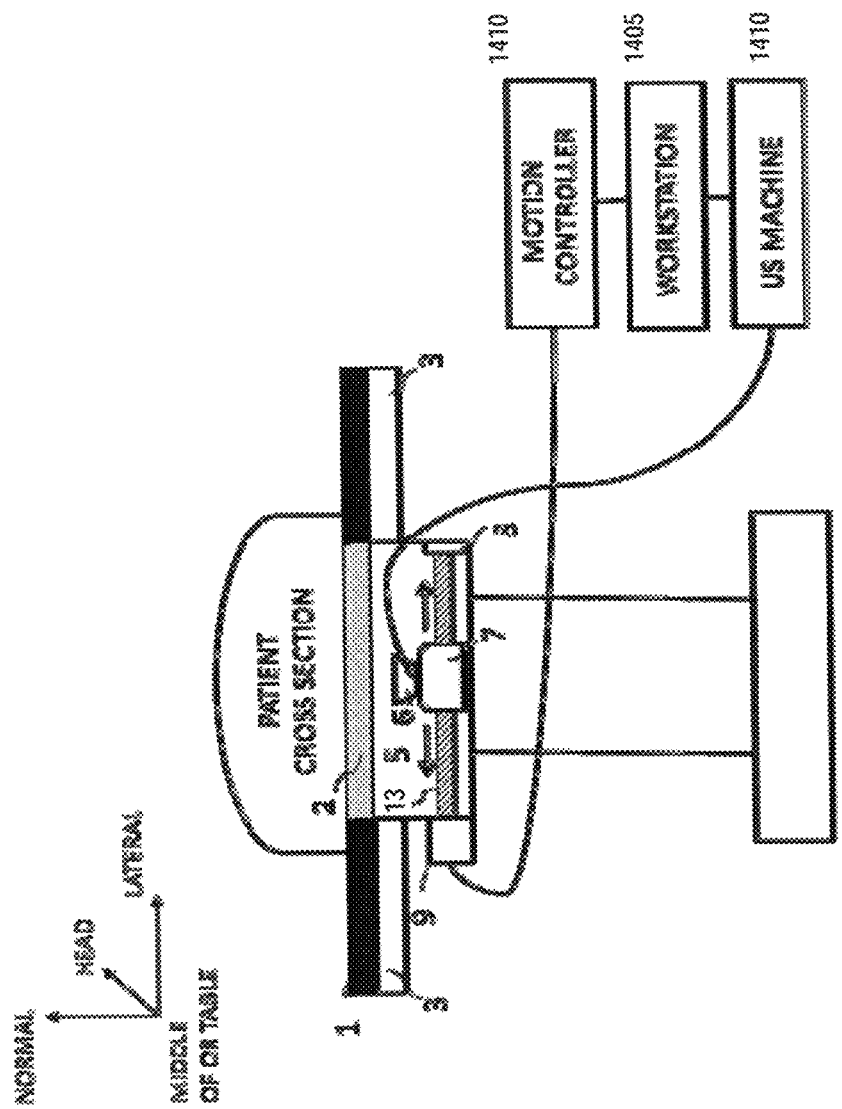
FIG. 15 illustrates a cross sectional view of an exemplary 3D ultrasound acquisition system with a linear array transducer, according to certain embodiments.

Next, FIG. 15 illustrates a cross sectional view of an exemplary 3D ultrasound acquisition system with a linear array transducer, according to certain embodiments.

In the tabletop volumetric ultrasound scanner setup, the SonoTable module is filled with a fluid 5 such as water or mineral oil so that ultrasound signal can travel through it. An ultrasound transducer 6 is mounted on a slider 7 moving on one or more linear stages (shafts) 13 that are fixed by a side support 8. A DC motor (or motors) 9 actuates user-defined or application-specific axial movement and an encoder connected to the DC motor electronically monitors the position of the rotating shaft 13. The scanner is capable of moving the transducer back and forth on the linear state. With linear scanning, parallel and equidistant 2D ultrasound images may be acquired that can then be stacked to form a volume.

The speed of the motor is determined by the desired physical spacing between consecutive slices and the ultrasound frame rate. Specifically, motor speed [mm/s]=spacing [mm]×frame rate [Hz].

Figure 16:
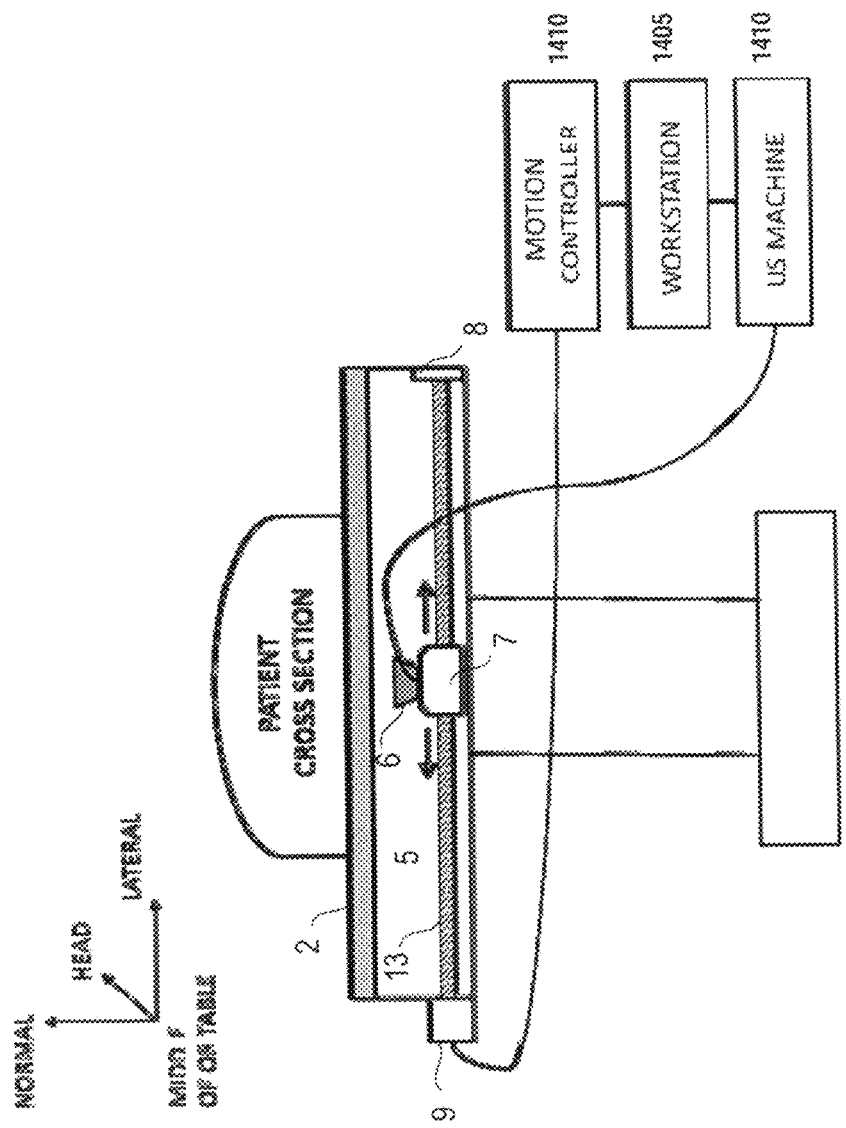
FIG. 16 illustrates a cross sectional view of an exemplary 3D ultrasound acquisition system with an extended range, according to certain embodiments.
Figure 17:
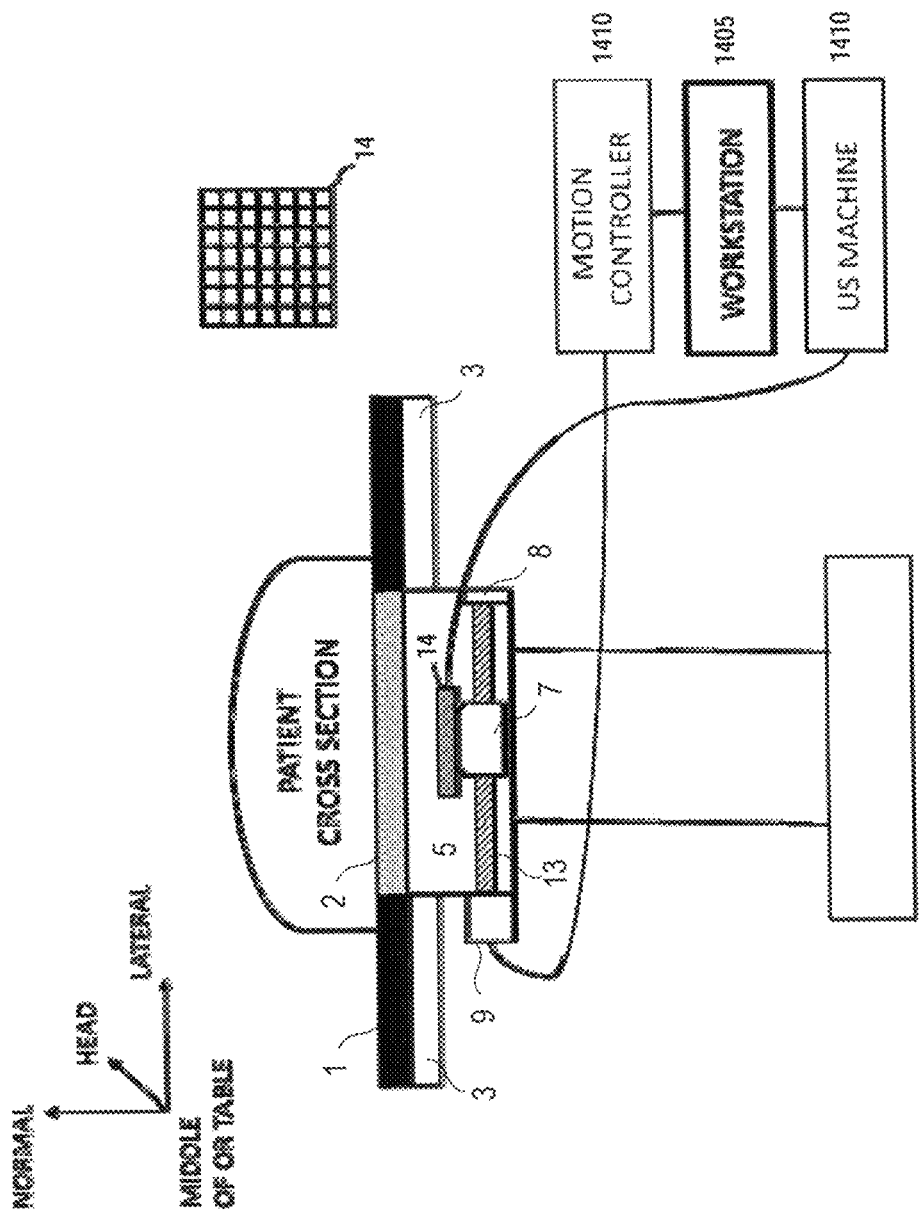
FIG. 17 illustrates a cross sectional view of an exemplary 3D ultrasound acquisition system with a matrix (3D) ultrasound transducer, according to certain embodiments.

In the system overview in FIG. 13, the SonoTable module is placed in the center of an OR table, where the abdomen of the patient is generally positioned. However, the range of scanning can be expanded to cover the entire width of the OR table to meet the needs of a variety of surgical procedures and to pick the desired imaging volume with greater flexibility, as shown in FIG. 16.

In other embodiments (e.g., FIG. 17), a matrix (or 3D) ultrasound transducer 14 may be implemented as part of the SonoTable modules, which could enable faster volume acquisition rates as well as the ability to reconstruct larger volumes.

The 3D ultrasound acquisition system according to the present disclosure includes a visualization module developed using a cross-platform application framework. The module displays three orthogonal planar views and a volume rendered view of the reconstructed volumetric ultrasound image. Furthermore, these views may be updated each time a new ultrasound volume becomes available. Because of the parallel nature of volume rendering (as well as most other rendering techniques), embodiments of the present disclosure utilize the power of general-purpose parallel computing on graphics processing units available in modern workstations for real-time performance.

Figure 18:
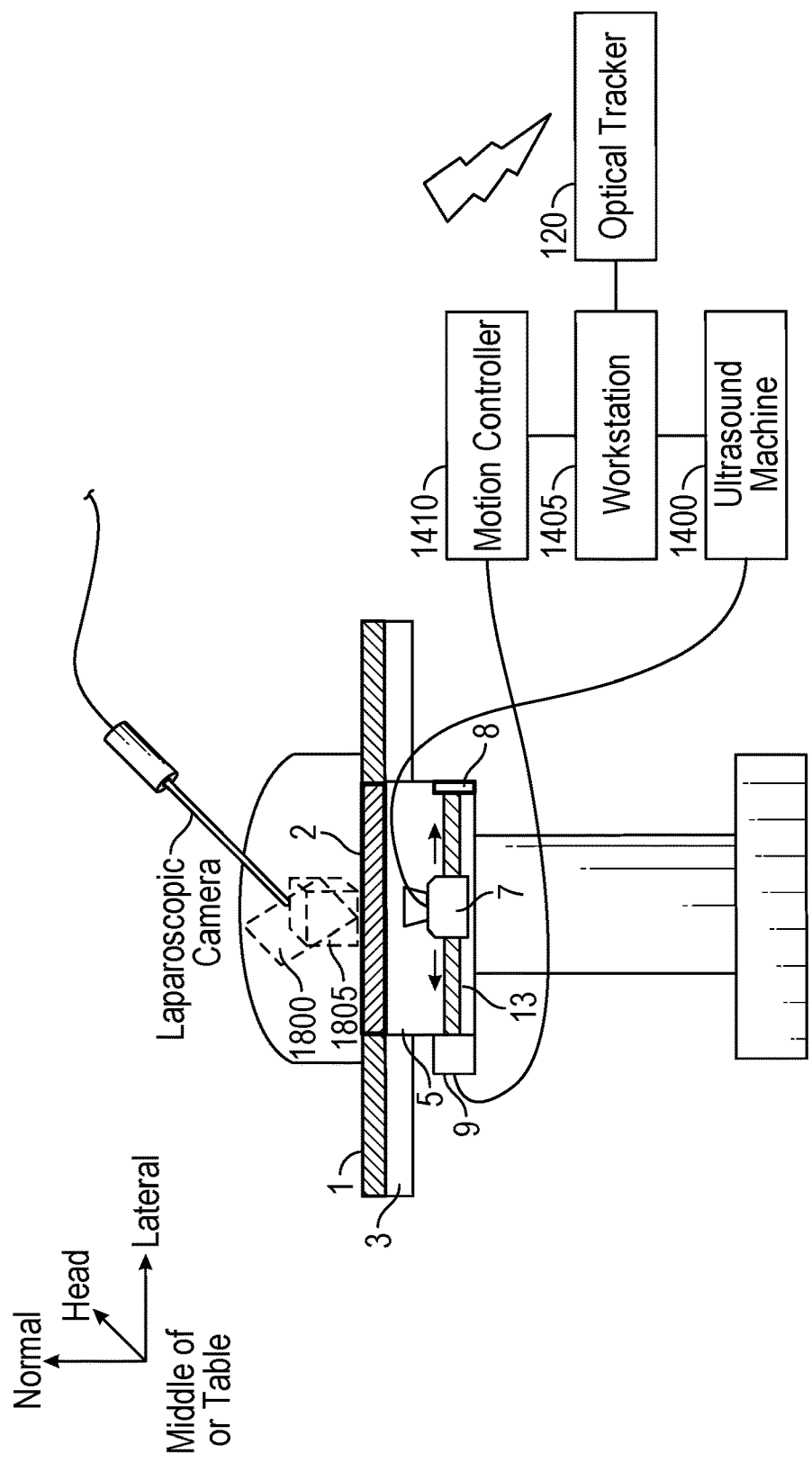
FIG. 18 illustrates an exemplary setup for multimodality visualization of the surgical anatomy during laparoscopic surgery, according to certain embodiments.

In FIG. 18, the combination of 3D ultrasound images with laparoscopic video is shown. Both imaging devices are spatially tracked. A projection image 1800 from the reconstructed ultrasound volume 1805 is rendered using the projection matrix of a laparoscopic camera and spatial tracking information generated by an optical tracker. Here, for generating an ultrasound projection image, the maximum intensity projection (MIP) technique may be used. As a rendering technique, MIP has been found helpful in the visualization of the vasculature, tumors, and lesions. The MIP is a volume rendering method that projects the voxel with the highest intensity value in the volume along each ray-case direction. To overlay MIP of the ultrasound volume onto laparoscopic video, the tracked position of the laparoscope camera with respect to the optical tracker is transformed to the coordinate of the ultrasound volume as $$P'(x^1) = (T_{LUS_{DRF}}^{LUS})^{-1} * (T_{tracker}^{LUS_{DRF}})^{-1} * T_{tracker}^{LAP_{DRF}} * T_{LAP_{DRF}}^{camera} * P(\vec{0})$$

where $P'(\vec{x})$ is the position of the laparoscopic camera in the coordinates of the ultrasound volume, $T_{LAP_{DRF}}^{camera}$ is the transformation from the laparoscopic camera to the laparoscope DRF, $T_{tracker}^{LAP_{DRF}}$ is the transformation from laparoscope DRF to the optical tracker, $T_{tracker}^{LUS_{DRF}}$ is the transformation from the ultrasound DRF to the tracker, and $T_{LUS_{DRF}}^{LUS}$ is the transformation from transducer to the ultrasound DRF. Note that the scale in the rotation matrix of ultrasound should be excluded from consideration. Among camera parameters, the focal point can be computed by finding the intersection point of the line extending from the laparoscope DRF to the camera with ultrasound imaging plane passing the center of the volume. The up vector for visualization is obtained by computing the vector of the laparoscope DRF with respect to the local coordinates. Therefore, a perspective transformation is obtained using intrinsic parameters encompassing focal length and principal point. The above procedure is repeated for left and right channels of the stereoscopic laparoscope. Next, two MIPs are generated for the two channels from the ultrasound volume using VTK (Kitware Inc., Clifton Park, N.Y., USA). Finally, these two MIPs are composited with the stereoscopic video images using alpha blending and displayed on a stereo monitor.

Usually the proximal and distal areas of the ultrasound images are bright because of the ring-down effect and strong reflections from the bottom surface of the water tank. It is therefore desirable to crop the top and bottom parts of the ultrasound volume before creating MIPs. This technique is called thin-slab MIP in which the user can select the ultrasound slab thickness and adjust the slab location in the original volume before volume rendering.

Figure 19:
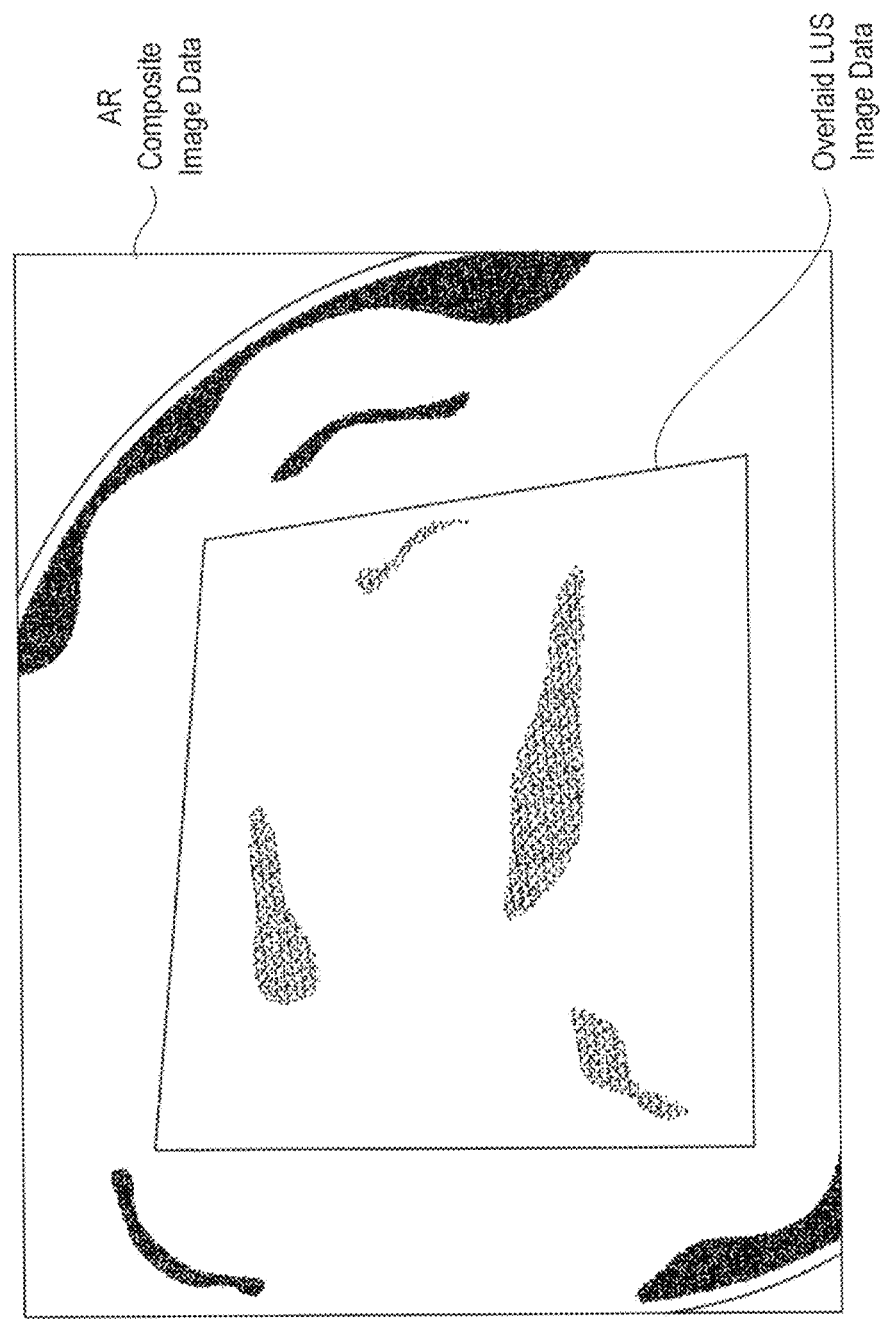
FIG. 19 illustrates an example of multimodality visualization showing an overlay of laparoscopic video image and volume rendering of reconstructed 3D ultrasound during a laparoscopic procedure using a stereoscopic AR system, according to certain embodiments.

If the video images are stereoscopic, the combined multimodality images may be viewed on a 3D monitor. FIG. 19 shows an example of a representative frame of such multimodality visualization in the standard (non-stereoscopic) format. The multimodality imaging enabled by the present disclosure can be used for needle-based ultrasound-guided laparoscopic interventions.

Figure 20:
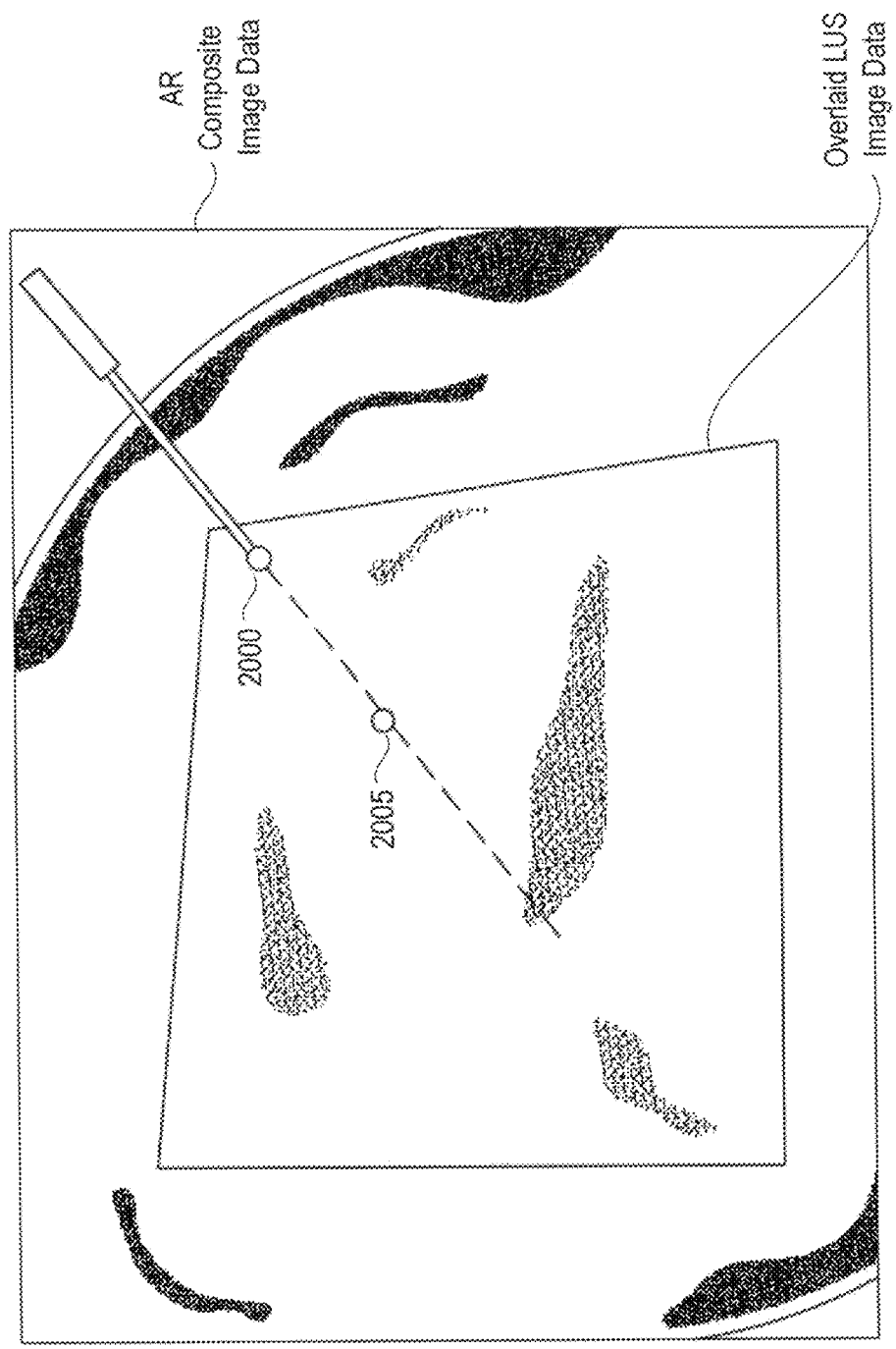
FIG. 20 illustrates an example of multimodality visualization showing overlay of laparoscopic video image, volume rendering of reconstructed 3D ultrasound, and projected needle path for guiding the interventional needle to the intended target during a laparoscopic procedure using a stereoscopic AR system, according to certain embodiments.

FIG. 20 shows a multimodality image of the surgical anatomy along with the projected path of a tracked interventional needle. The intersection of the needle path and the ultrasound plane is computed and presented as a navigation aid. This form of visualization enabled by the present disclosure has the potential to improve the precision of laparoscopic ablations, biopsies, drainages, aspirations, therapeutic delivery, vascular access, and anesthesia delivery. FIG. 20 includes navigational guidance overlaid on the AR composite image data to aid the surgeon performing the procedure. In the exemplary embodiment of FIG. 20, a marker 2000 and 2005 respectively indicate an entry position and a target position.

Next, FIG. 21 illustrates an exemplary velocity profile of the DC motor 9 during image capture. Referring to the figure, during intervals A and C, image series are stacked to build an ultrasound volume except that in interval C the stack is reversed as the motor moves in the opposite direction. During interval B, which is the time when the motor is ramping up and down, the stack is written to VTK image data, representing a geometrical structure including a volume, for visualization.

EXPERIMENTAL RESULTS

A series of experiments were conducted using a system consistent with embodiments discussed above with respect to FIGS. 13-21. Results of the experiments follow below.

System Evaluation

High ultrasound image-to-laparoscopic video registration accuracy and low system latency are desirable for a successful clinical AR visualization system. Any registration error will cause misalignment of anatomical structures between the two imaging modalities involved in AR visualization and make surgeries based on such visualization unsafe. A long time delay between the motion of the ultrasound transducer and the corresponding images presented to the surgeons will affect the real-time interaction and visual feedback necessary for surgical efficiency and effectiveness.

The accuracy of the overall AR system relies on the calibration accuracy of the stereoscopic laparoscope as well as the drop-in ultrasound transducer, and the accuracy of the stereoscopic AR visualization. The TRE metric was used to measure the accuracies of these components. Experiments were conducted using a cross-wire phantom, with the intersection of the two wires as the target point. The TRE is defined as the Euclidean distance between the actual 3D location known by touching the intersection point with a tracked pointer and the computed 3D location determined through triangulation of the identical points in a pair of images. The calibration accuracies of the stereoscopic laparoscope, the drop-in ultrasound transducer, and the overall AR visualization accuracy were measured to be 0.93±0.21 mm, 3.52±1.16 mm and 4.04±1.00 mm, respectively.

The system latency was measured by imaging a high-resolution (millisecond) digital clock. The difference between the actual clock time and the time seen in the AR output image of our system determines the system latency. To account for all delays, the stereoscopic AR system was operated in the full-function mode with simultaneous laparoscopic ultrasound imaging. The overall system latency was measured to be 195±10 ms. This includes the latencies of the laparoscopic video and ultrasound imaging systems as well as those of data streaming through Ethernet, volume reconstruction and stereoscopic AR visualization computation.

Volume Reconstruction

Reconstruction of the ultrasound volume includes reconstruction from the stack of parallel, sequentially acquired ultrasound slices. Because linear scanning in a 3D ultrasound system according to embodiments of the present disclosure is predefined and precisely controlled by the motion controller, the relative position of the acquired 2D ultrasound slices is known. Experiments were conducted on a conventional cross-wire phantom (70 mm wide, 50 mm high) submerged in a water tank. At a streaming rate of 30 Hz, ultrasound images were acquired with a resolution of 780×800 with a pixel size of 0.07 mm×0.07 mm.

The tests included two different slice spacing settings of 0.2 mm and 0.1 mm with the goal of assessing the quality of volume reconstruction by observing the presence or absence of any staircase effect in the reconstructed volume. For the two settings, the corresponding motor speeds were 6 mm/s and 3 mm/s and it took 12 seconds and 23 seconds to complete 3D scanning of the phantom. The resulting longitudinal view of the reconstructed 3D ultrasound volume exhibited good reconstruction quality (i.e., wires appeared as straight lines). The smaller slice spacing (0.1 mm), as expected, yielded better quality with no staircase artifact.

Phantom Study

A phantom study was performed using a realistic intra-operative abdominal ultrasound phantom (IOUSFAN, Kyoto Kagaku Co. Ltd., Kyoto, Japan). The ultrasound volume was reconstructed with a slice spacing of 0.2 mm. Accordingly, a scanned volume of 104 mm×101 mm×71 mm was acquired, including anatomical structures such as vasculatures and tumors. With the streaming rate of 30 Hz and the motor speed of 6 mm/s, approximately 12 seconds were needed to complete a volume sweep. The thin-slab MIP image was created so as to remove the top of the volume as that portion obscured the view of the critical anatomy (i.e., the anatomy of interest). The resulting overlay of the MIP of the ultrasound volume with the stereoscopic video exhibited good alignment.

Obviously, numerous modifications and variations of the present disclosure are possible in light of the above teachings. It is therefore to be understood that within the scope of the appended claims, the invention may be practiced otherwise than as specifically described herein. For example, advantageous results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable processing circuits configured to execute program code and/or computer instructions to execute the functions, processes and algorithms described herein. A processing circuit includes a programmed processor, as a processor includes circuitry. A processing circuit also includes devices such as an application specific integrated circuit (ASIC) and conventional circuit components arranged to perform the recited functions.

The functions and features described herein may also be executed by various distributed components of a system. For example, one or more processors may execute these system functions, wherein the processors are distributed across multiple components communicating in a network. The distributed components may include one or more client and/or server machines, in addition to various human interface and/or communication devices (e.g., display monitors, smart phones, tablets, personal digital assistants (PDAs)). The network may be a private network, such as a LAN or WAN, or may be a public network, such as the Internet. Input to the system may be received via direct user input and/or received remotely either in real-time or as a batch process. Additionally, some implementations may be performed on modules or hardware not identical to those described. Accordingly, other implementations are within the scope that may be claimed.

It must be noted that, as used in the specification and the appended claims, the singular forms "a," "an," and "the" include plural referents unless the context clearly dictates otherwise.

The invention claimed is:

1. A stereoscopic augmented reality (AR) system for generating real-time composite images of dynamically-changing surgical anatomy obtained during a surgery, the stereoscopic AR system comprising:

a display;
an endoscopic imaging device that generates endoscopic image data during the surgery;
a tomographic imaging device that generates intra-operative tomographic image data during the surgery;
a tracking device that tracks a position and an orientation of the endoscopic imaging device and the tomographic imaging device in real-time during the surgery and generates, based on the position and the orientation of the devices, spatial tracking data corresponding to each of the endoscopic imaging device and the tomographic imaging device in real-time during the surgery, the tracking device including
a first tracking marker,
a first sterilizable rigid mount removably coupled to the endoscopic imaging device,
a second tracking marker, and
a second sterilizable rigid mount removably coupled to the tomographic imaging device; and
processing circuitry configured to
receive during the surgery, from the endoscopic imaging device, the endoscopic image data,
receive during the surgery, from the tomographic imaging device, the intra-operative tomographic image data,
receive during the surgery, from the tracking device, the spatial tracking data corresponding to the endoscopic imaging device and the tomographic imaging device, generate, during the surgery, real-time dynamically-changing composite image data by overlaying, based on the spatial tracking data, the intra-operative tomographic image data with the endoscopic image data, and output in real time, during the surgery, the real-time dynamically-changing composite image data having the intra-operative tomographic image data overlain with the endoscopic image data to the display for output as a live stereoscopic AR view of an operating environment associated with the dynamically-changing surgical anatomy, wherein the outputted real-time dynamically-changing composite image data is in the form of two tomographic-augmented video streams that produce the live stereoscopic AR view of the operating environment associated with the dynamically-changing surgical anatomy and the surgery, the first sterilizable rigid mount is removably coupled to the endoscopic imaging device to be slidable from a distal end of the endoscopic imaging device toward a proximal end of the endoscopic imaging device in order to be at a first same predetermined position, the first sterilizable rigid mount surrounding a longitudinal axis of the endoscopic imaging device, the first tracking marker being attached to a side projection of the first sterilizable rigid mount at the first same predetermined position relative to the first sterilizable rigid mount and the endoscopic imaging device, the second sterilizable rigid mount is removably coupled to the tomographic imaging device to be slidable from a distal end of the tomographic imaging device toward a proximal end of the tomographic imaging device in order to be at a second same predetermined position, the second sterilizable rigid mount surrounding a longitudinal axis of the tomographic imaging device, the second tracking marker being attached to a side projection of the second sterilizable rigid mount at the second same predetermined position relative to the second sterilizable rigid mount and the tomographic imaging device, and the first tracking marker and the second tracking marker at the first same predetermined position and the second same predetermined position, respectively, are tracked using the spatial tracking performed by the tracking device without recalibrating the endoscopic imaging device and the tomographic imaging device.

2. The system of claim 1, wherein the tomographic imaging device is implemented within an operating table.

3. The system of claim 1, wherein the tomographic imaging device is configured to generate the intra-operative tomographic image data by hands-free operation.

4. The system of claim 1, wherein:
the intra-operative tomographic image data corresponds to an internal anatomy of a patient, and
the tomographic imaging device is configured to generate the intra-operative tomographic image data by capturing the intra-operative tomographic image data externally from the patient.

5. The system of claim 1, wherein:
the intra-operative tomographic image data is two dimensional; and
the processing circuitry is further configured to
generate volumetric tomographic image data based on the intra-operative tomographic image data and the spatial tracking data, and
generate the composite image data by overlaying, based on the spatial tracking data, the volumetric tomographic image data on the endoscopic image data.

6. The system of claim 1, wherein the tracking device is one of an optical tracking device and an electro-magnetic tracking device.

* * * * *